US005612318A

United States Patent [19]
Weichselbaum et al.

[11] Patent Number: 5,612,318
[45] Date of Patent: *Mar. 18, 1997

[54] CONTROL OF GENE EXPRESSION BY IONIZING RADIATION

[76] Inventors: Ralph R. Weichselbaum, 2031 N. Sedgwick, Chicago, Ill. 60616; Dennis E. Hallahan, 5343 N. Moody, Chicago, Ill. 60630; Vikas P. Sukhatme, 1511 E. 56th St., Chicago, Ill. 60637; Donald W. Kufe, 179 Grove St., Wellesley, Mass. 02181

[*] Notice: The term of this patent shall not extend beyond the expiration date of Pat. No. 5,571,797.

[21] Appl. No.: 212,308

[22] Filed: Mar. 14, 1994

Related U.S. Application Data

[63] Continuation of Ser. No. 35,897, Mar. 16, 1993, abandoned, which is a continuation of Ser. No. 633,626, Dec. 20, 1990, abandoned.

[51] Int. Cl.$^6$ .................................................. K61K 48/00
[52] U.S. Cl. ........................ 514/44; 435/172; 435/172.3; 435/240.2; 536/24.1; 935/34
[58] Field of Search .................................. 536/23.1, 24.1, 536/23.5, 23.51; 435/69.1–69.7, 320.1; 514/44; 424/1.73, 1.11; 935/34

[56] References Cited

U.S. PATENT DOCUMENTS 4,677,063  6/1987  Mark et al. ............................... 435/68

FOREIGN PATENT DOCUMENTS

WO92/11033  12/1991  WIPO.

OTHER PUBLICATIONS

Christy et al. 1988. P.N.A.S. 85:7857–7861.
Angel et al. 1988. Cell. 55:875–885.
Sambrook et al. 1989 Molecular Cloning–A Laboratory Manual. CSH Laboratory Press, CSH, NY p. 16.5.
Miller et al (1995) FASEBJ 9 190–199.
Culver et al (1994) Trends in Genetics 10:174–178.
Hodgson (1995) Exp Opin Ther Patents 5: 459–468.
Marshall (1995) Science 269:1050–1055.
Sherman et al 1990. PNAS 87: 5663–5666.
Moffet — Applicants' submission of a newspaper article.
Seisa et al 1988 Int. J. Cancer. 42:129–134.
Baichwal, V.R. and Tjian, R., v–Src and EJ Ras Alleviate Repression of c–Jun by a Cell–Specific Inhibitor, *Nature*, 352:165–168, 1991.
Baichwal, V.R. and Tjian, R., Control of c–Jun Activity by Interaction of a Cell–Specific Inhibitor with Regulatory Domain δ:Differences between v– and c–Jun, *Cell. Vol.*, 63:815–825, 1990.
Binetruy et. al, Ha–Ras augments c–Jun activity and stimulates phosphorylation of its activation domain, *Nature*, 351:122–127, 1991.
Boothman et. al, Identificatin and Characterization of X–Ray induced Proteins in Human Cells, *Cancer Res.*, 49:2871–2878, 1989.
Borek, C., The Induction and Control of Radiogenic Transformation In Vitro: Cellular and Molecular Mechanisms, *Pharmacol. Ther.*, 27:99–143, 1985.

(List continued on next page.)

Primary Examiner—Bruce R. Campell
Attorney, Agent, or Firm—Arnold, White & Durkee

[57]  ABSTRACT

This invention relates to genetic constructs which comprise an enhancer-promoter region which is responsive to radiation, and at least one structural gene whose expression is controlled by the enhancer-promoter. This invention also relates to methods of destroying, altering, or inactivating cells in target tissue by delivering the genetic constructs to the cells of the tissues and inducing expression of the structural gene or genes in the construct by exposing the tissues to ionizing radiation. This invention is useful for treating patients with cancer, clotting disorders, myocardial infarction, and other diseases for which target tissues can be identified and for which gene expression of the construct within the target tissues can alleviate the disease or disorder.

8 Claims, 16 Drawing Sheets

OTHER PUBLICATIONS

Datta et. al, Ionizing radiation activates transcription of the *EGR1* gene via CArG elements, *Proc. Natl. Acad. Sci. USA*, 89:10149–10153, 1992.

Dewey, W.C., In Vitro Systems: Standarization of Endpoints, *Int. J. Radiation Oncology Biol. Phys.*, 5:1165–1174, 1979.

Eocnomou et. al, Genetic Analysis of the Human Tumor Necrosis Factor α/Cachectin Promoter Region in a Macrophage Cell Line, *J. Exp. Med.*, 170:321–326, 1989.

Fornace et. al, Induction of β–Polymerase mRNA by DNA–Damaging Agents in Chinese Hamster Ovary Cells, *Mol. Cell. Biol.*, 9:851–853, 1989.

Fornace et. al, DNA damage–inducible transcripts in mammalian cells, *Proc. Natl. Acad. Sci. USA*, 85:8800–8804, 1988.

Gilman, M., The c–fos serum response element responds to protein kinase C–dependent and –independent signals but not to cyclis AMP, *Genes Dev.*, 2:394–402, 1988.

Guis et. al, Transcriptional Activation and Repression by Fos Are Independent Functions: The C Terminus Represses Immediate–Early Gene Expression via CArG Elements, *Mol. Cell. Biol.*, 10:4243–4255, 1990.

Gupta et. al, Egr–1, a Serum–inducible Zinc Finger Protein, Regulates Transcription of the Rat Cardiac α–Myosin Heavy Chain Gene*, *J. Biol. Chem.*, 266:12813–12816, 1991.

Hall, E.J., in *Radiobiology for the Radiologist*, ed. Hall, E.J. (Lippincott, Philadelphia), pp. 17–38, 1988.

Hallahan et. al, Tumor Necrosis Factor Gene Expression Is Mediated by Protein Kinase C following Activation by Ionizing Radiation, *Cancer Res.*, 51:4565–4569, 1991.

Hallahan et. al, Protein kinase C mediates x–ray inducibility of nuclear signal transducers EGR1 and JUN, *Proc. Natl. Acad. Sci. USA*, 88:2156–2160, 1991.

Hallahan et. al, Transcriptional regulation of the TNF gene by x–irradiation, *Proc. Am. Assoc. Cancer Res.*, vol. 31, No. 0, Mar. 1990, p. 75, #448.

Homma et. al, Translocation of protein kinase C in human leukemia cells susceptible or resistant to differentiation induced by phorbol 12–myristate 13acetate, *Proc. Natl. Acad. Sci. USA*, 83:7316–7319, 1986.

Little, J.W., and Mount, D.A., The SOS Regulatory System of *Escherichia coli*, *Cell.*, 29:11–22, 1982.

Miskin, R. and Ben–Ishai, R., Induction of plasminogen activator by UV light in normal and xeroderma pigmentosum fibroblasts, *Proc. Natl. Acad. Sci. USA*, 78:(10)6236–6240, 1981.

Pulverer et. al, Phosphorylation of c–jun mediated by MAP kinases, *Nature*, 353:670–674, 1991.

Rorsman et. al, Structural Characterization of the Human Platelet–Derived Growth Factor A–Chain cDNA and Gene: Alternative Exon Usage Predicts Two DIfferent Precusor Proteins, *Mol. Cell. Biol.*, 8:571–577, 1989.

Sherman et. al, Regulation of Tumor Necrosis Factor Gene Expression by Ionizing Radiation in Human Myeloid Leukemia Cells and Peripheral Blood Monocytes, *J. Clin. Invest.* 87:1794–1797, 1991.

Hallahan et al., *Int. J. Radiation Oncology Biol. Phys.* 19:69–74, 1990.

Hallahan et al., *PNAS*, 86:10104–10107, 1989.

Simon Moffat — A newspaper report.

Witte et al., *Cancer Res.*, 49(18):5066, Abstract, 1989.

Fornace et al., *Mol. Cell. Biol.*, 8(11) :4716–4720, 1988.

Dialog Search Report.

Sherman et al., "Ionizing radiation regulates expression of the c–jun proto–oncogene," *Proc. Am. Assoc. Cancer Res.*, 31(0) :13, 1990.

Hallahan et al., "Transcriptional regulation of the TNF gene by x–irradiation," *Proc. Am. Assoc. Cancer Res.*, 31(0):75, 19990.

Sherman et. al, Transcriptional and Post–transcriptional Regulation of c–jun Expression during Monocytic DIfferentiation of Human Myeloid Leukemic Cells, *J. Biol. Chem.*, 265:3320–3323, 1990.

Sherman et. al, Ionizing radiation regulates expression of the c–jun proto–oncogene, *Proc. Am. Assoc. Cancer Res.*, vol. 31, No. 0, Mar. 1990, p. 13, #76.

Sukhatme et. al, A Zinc Finger–Encoding Gene Coregulated with c–fos during Growth and Differentiation, and after Cellular Depolarization, *Cell*, 53:37–43, 1988.

Sukhatme et. al, A Novel Early Growth Response Gene Rapidly Induced by Fibroblast, Epithelial Cell and Lymphocyte Mitogens, *Oncogene*, 1:343–355, 1987.

Weichselbaus et. al, In Vitro Radiobiological Parameters of Human Sarcoma Cell Lines, *Int. J. Radiation Oncology Biol. Phys.*, 15:937–942, 1988.

Witte et. al, Effects of Irradiation on the Release of Growth Factors from Cultured Bovine, Porcine, and Human Endothelial Cells, *Cancer Res.*, 49:5066–5072, 1989.

Woloschak et. al, Modulation of Gene Expression in SYrian Hamster Embryo Cells following Ionizing Radiation, *Cancer Res.*, 50:339–344, 1990.

European Search Report, Mailed Dec. 16, 1993.

International Search Report, Mailed Dec. 17, 1993.

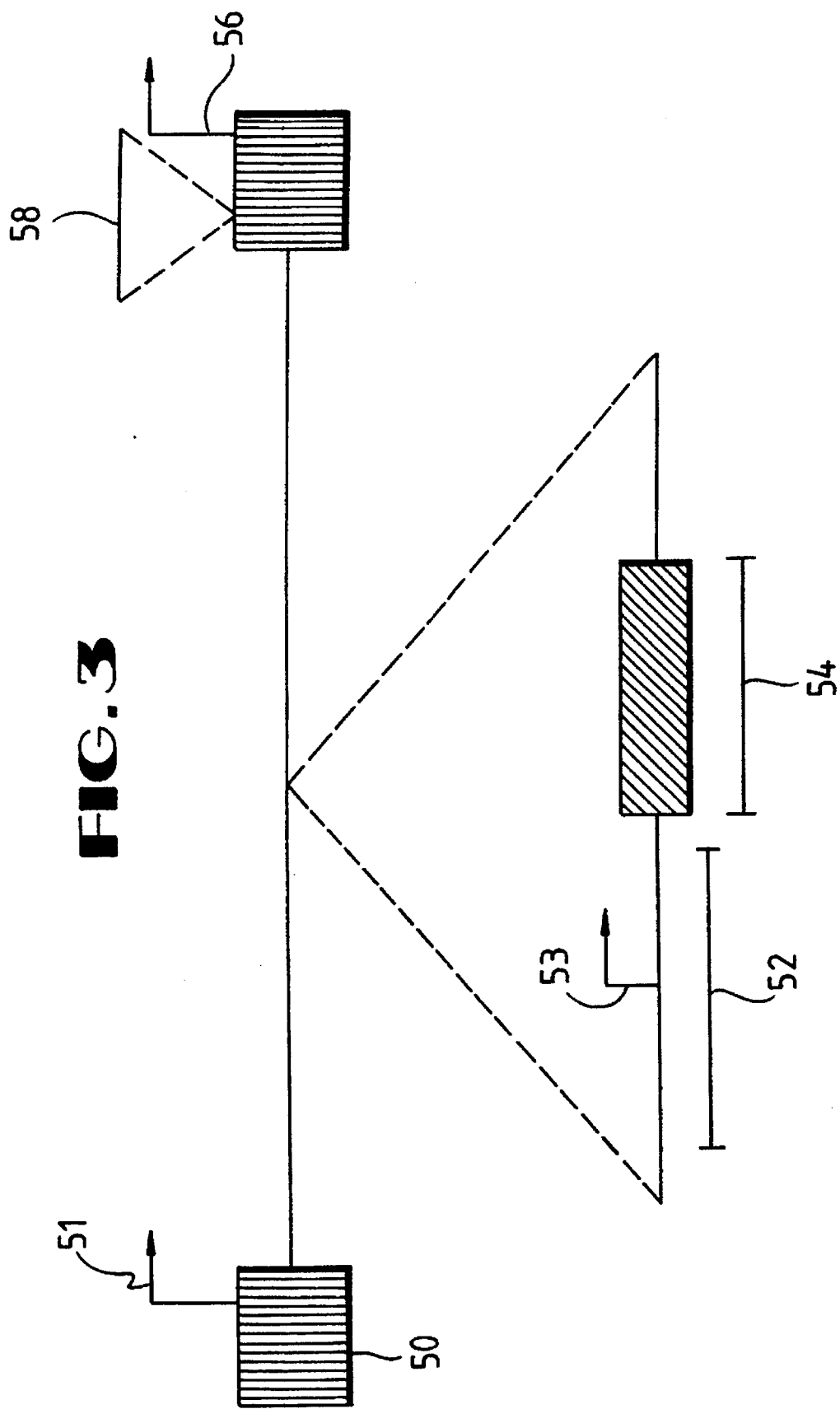

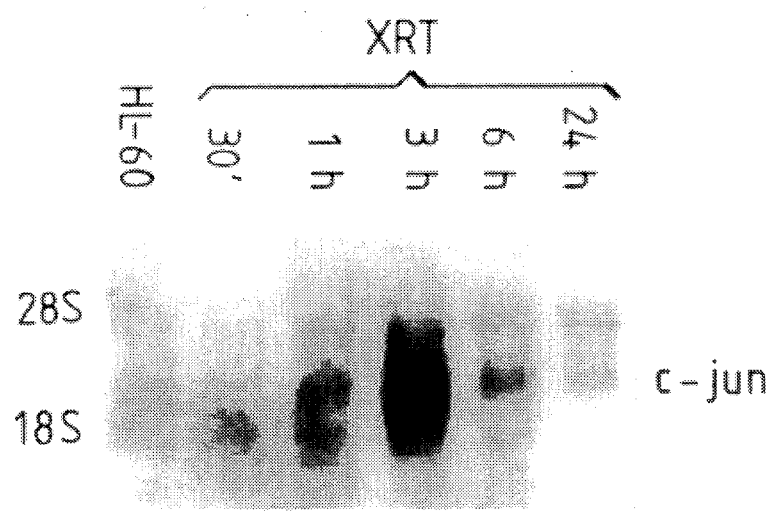
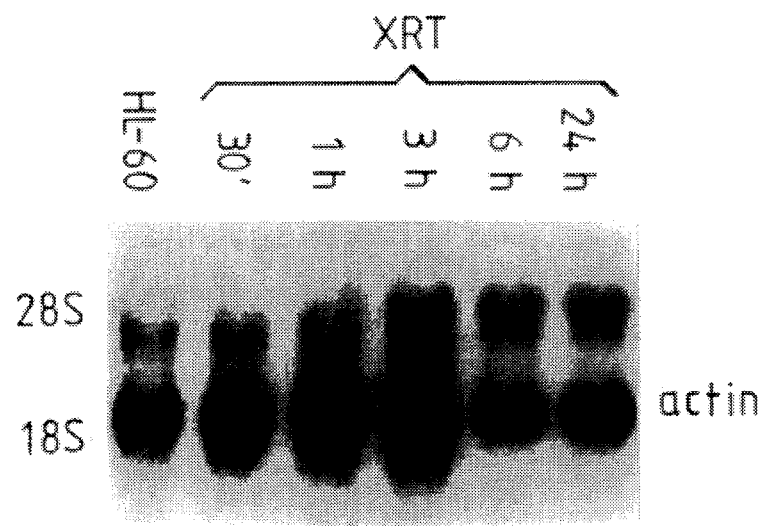

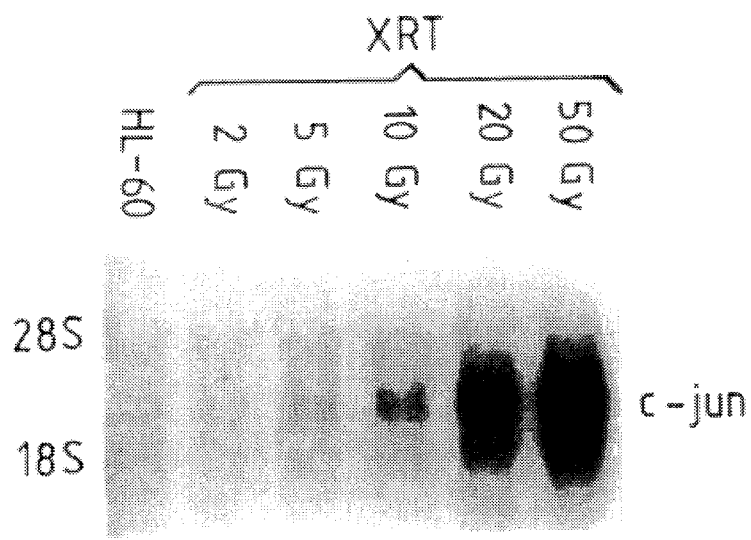
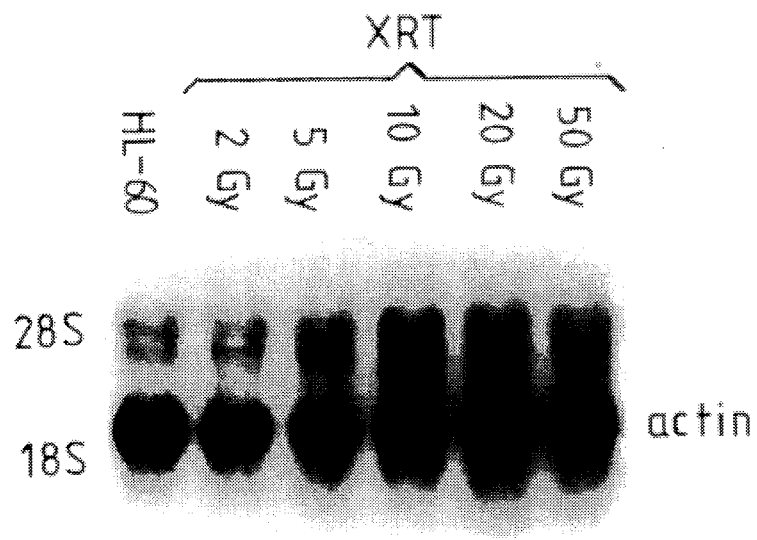

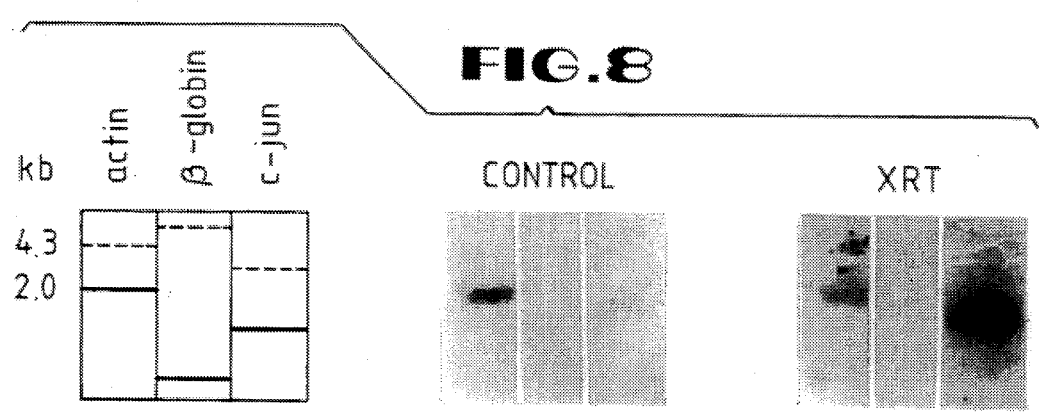

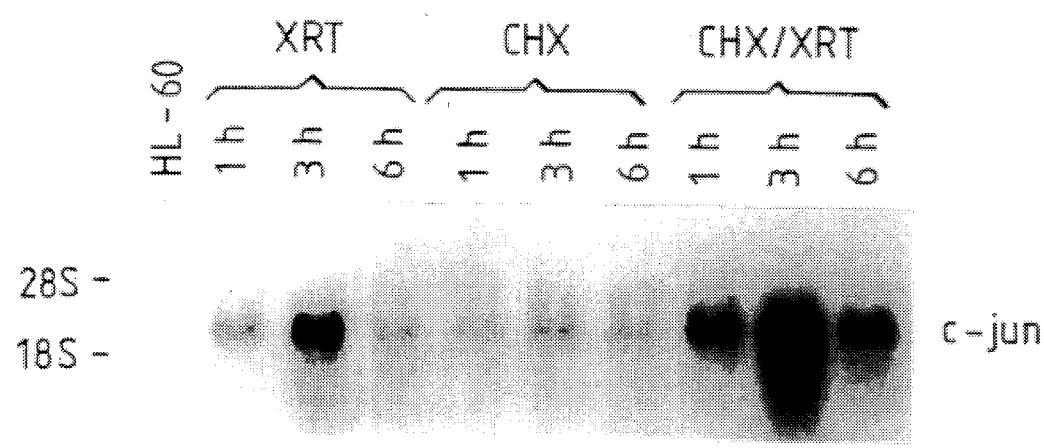

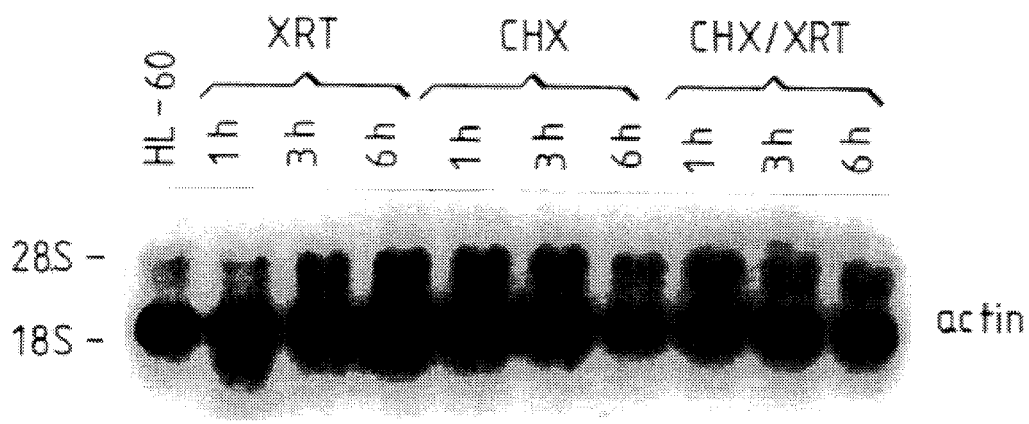

CONTROL OF GENE EXPRESSION BY IONIZING RADIATION

The U.S. Government may own rights in the present invention pursuant to NIH Grant No. RO1 CA41068, RO1 CA42596 and CA58508.

This application is a continuation of application Ser. No. 08/035,897, filed Mar. 16, 1993, abandoned, which is a continuation of No. 07/633,626, filed Dec. 20, 1990, abandoned.

BACKGROUND OF THE INVENTION

1. Field of the Invention

This invention relates to methods of controlling gene expression by radiation responsive genetic constructs. This invention also relates to methods and compositions for destroying, altering, or inactivating target tissues. These tissues may be disease-related, for example, tumors, or blood clots, or they may have a metabolic deficiency or abnormality. An aspect of this invention is to deliver radiation responsive genetic constructs to target tissues and to activate the genes in said constructs by exposing the tissues to external ionizing radiation.

2. Description of the Related Art

Certain genes may play a role in the cellular response to stress or DNA-damaging agents. For example, metallothionein I and II, collagenase, and plasminogen activator are induced after UV irradiation (Angel, et al., 1986; 1987; Fornace, et al., 1988a and b; Miskin, et al., 1981). B2 polymerase III transcripts are increased following treatment by heat shock (Fornace, et al., 1986; 1989a). Furthermore, although the level of DNA polymerase β mRNA is increased after treatment with DNA-damaging agents, this transcript is unchanged following irradiation, suggesting that specific DNA-damaging agents differentially regulate gene expression (Fornace, et al., 1989b). Protooncogene c-fos RNA levels are elevated following treatment by UV, heat shock, or chemical carcinogens (Andrews, et al., 1987; Hollander, et al., 1989a). In this regard, the relative rates of fos transcription during heat shock are unchanged, suggesting that this stress increased c-fos RNA through posttranscriptional mechanisms (Hollander, et al., 1989b).

Investigations of the cytotoxic effects of ionizing radiation have focused on the repair of DNA damage or the modification of radiation lethality by hypoxia (Banura, et al., 1976; Moulder, et al., 1984). In prokaryotes and lower eukaryotes, ionizing radiation has been shown to induce expression of several DNA repair genes (Little, et al., 1982); however, induction of gene expression by ionizing radiation has not been described in mammalian cells. DNA-damaging agents other than x-rays induce expression of a variety of genes in higher eukaryotes (Fornace, et al., 1988, 1989; Miskin, et al., 1981).

What is known about the effects of ionizing radiation is that DNA damage and cell killing result. In many examples, the effects are proportional to the dose rate. Ionizing radiation has been postulated to induce multiple biological effects by direct interaction with DNA or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985).

Several studies have described changes in the pattern of protein synthesis observed after irradiation of mammalian cells. For example, ionizing radiation treatment of human malignant melanoma cells is associated with induction of several unidentified proteins (Boothman, et al., 1989). Synthesis of cyclin and coregulated polypeptides is suppressed by ionizing radiation in rat REF52 cells but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

Initiation of mRNA synthesis by DNA is a critical control point in the regulation of cellular processes and depends on bindings of certain transcriptional regulatory factors to specific DNA sequences. However, little is known about the regulation of transcriptional control by ionizing radiation exposure in eukaryotic cells. The effects of ionizing radiation on posttranscriptional regulation of mammalian gene expression are also unknown.

Many diseases, conditions, and metabolic deficiencies would benefit from destruction, alteration, or inactivation of affected cells, or by replacement of a missing or abnormal gene product. In certain situations, the affected cells are focused in a recognizable tissue. Current methods of therapy which attempt to seek and destroy those tissues, or to deliver necessary gene products to them, have serious limitations. For some diseases, e.g., cancer, ionizing radiation is useful as a therapy. Methods to enhance the radiation, thereby reducing the necessary dose, would greatly benefit cancer patients. Therefore, methods and compositions were sought to enhance radiation effects by investigating effects of radiation on gene expression. A goal was to provide new types of therapy using radiation, and to explore other uses of radiation.

SUMMARY OF THE INVENTION

In this invention, control exerted over gene expression by a promoter-enhancer region, which is responsive to ionizing radiation, is used as a switch to selectively introduce gene products to distinct tissue targets, providing opportunities for therapeutic destruction, alteration, or inactivation of cells in target tissues. These promoter-enhancer regions control gene expression through application of a radiation trigger.

More particularly, this invention relates to methods and compositions for treating diseases and conditions for which destruction, alteration or inactivation of cells in affected tissues would alleviate the disease or condition. The methods comprise delivering a genetic construct to cells of the host tissue and subsequently exposing the tissue to ionizing radiation. A region of the genetic construct is capable of being induced by ionizing radiation. Exposing the tissue to ionizing radiation, therefore, induces the expression of the genetic construct. The gene product is then capable of destroying, altering, or inactivating the cells in the tissue. The gene product chosen for treatment of factor deficiencies or abnormalities, is one that provides the normal factor.

An illustrative embodiment of the genetic construct comprises a combination of a radiation responsive enhancer-promoter region and a region comprising at least one structural gene. The enhancer-promoter region drives the expression of a structural gene in the form of a reporter-effector gene appropriate for the disease or condition in the host.

The general composition of the construct comprises a radiation inducible promoter-enhancer region and a structural gene region. In an illustrative embodiment, the promoter is 5' to the structural gene region. In this embodiment, amplification of the final response does not occur. Rather there is a direct correlation between regulation of the radiation sensitive region and the structural gene. The inducible region is turned on by radiation exposure, but will turn off at some point after the radiation exposure ceases. Expression of the structural gene region is limited by exposure time and the inherent quantitative limits of the expression region.

In a preferred embodiment, to amplify the expression of the gene construct and to extend expression beyond exposure time, a cascade of promoters and expressing genes are contemplated, for example, two plasmids. The first plasmid comprises the radiation sensitive promoter 5' of an appropriate transcription factor. In an embodiment of a transcription factor, the first plasmid comprises a powerful activation domain, for example, that obtained from the herpes virus VP16. This domain contains many negatively charged residues. A chimeric protein is contemplated in this embodiment comprising the VP16 activation domain and a DNA binding domain of a known protein, for example, the lac repressor. The chimeric protein/gene construct (a fusion gene) is driven from a radiation sensitive promoter.

The second plasmid construct in the preferred embodiment comprises several binding sites for the lac repressor DNA binding domain. These binding sites are placed upstream of a reporter-effector gene, for example, TNF. Alternatively, the two plasmids described above could be merged into one construct.

The use of a cascade of promoters and two expressing genes as the genetic construct has several advantages:

(1) the promoter does not have to provide strong activation because amplification of the initial radiation sensitive promoter effect is provided through action of the subsequent genetic cascade;

(2) several genes may be included in the construct to provide more complex or more extensive action. In an illustrative embodiment, several toxin producing genes may be placed 3' of the appropriate DNA binding sites. An embodiment of a multiple gene construct comprises the DNA binding domain of the lac repressor followed by several genes which produce various regulators of cell growth; and (3) the effect due to the initial ionizing radiation may be temporarily prolonged; that is, if the half-life of the chimeric lac repressor protein were long, for example, hours or days, compared to the radiation exposure time during which promoter RNA is released, the effect of the genetic construct on the cell is prolonged.

The genetic construct of this invention is incorporated into the cells of a target tissue by any method which incorporates the construct without inhibiting its desired expression and control over that expression by radiation. These methods comprise electroporation, lipofection, or retroviral methodology.

Retroviruses used to deliver the constructs to the host target tissues generally are viruses in which the 3' LTR (linear transfer region) has been inactivated. That is, these are enhancerless 3'LTR's, often referred to as SIN (self-inactivating viruses) because after productive infection into the host cell, the 3'LTR is transferred to the 5' end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell, e.g., LAK cells.

For purposes of this invention, a radiation responsive enhancer-promoter which is 5' of the appropriate structural gene region, for example, a lymphokine gene, or a transcriptional activator, may be cloned into the virus.

The constructs are delivered into a host by any method that causes the constructs to reach the cells of the target tissue, while preserving the characteristics of the construct used in this invention. These methods comprise delivering the construct by intravenous injection, injection directly into a target tissue, or incorporation into cells which have been removed from the host. In the latter case, after in vitro incorporation of the constructs into the recipient cells, the cells containing the construct are reintroduced into the host. Depending on the type of recipient cell, the distribution of the cells in the host will vary—in some cases being focused to a specific area, for example, where cells are directed to a tumor or clot, in other cases diffusing through an entire system such as the bone marrow. Even when the cells carrying the genetic construct have dispersed over a wide area of the host, focusing the desired action of the construct on a target tissue can be provided by directing the ionizing radiation used to switch on the construct, to a limited area. Only the cells within the beam will react and cause expression of the construct genes.

Another method of focusing the genetic action of the construct, or homing it into particular body regions, is to tag the construct with a radioisotope or other label and determine when the construct bearing cells have reached the target tissue by detecting the label geographically. The radiation is turned on when the construct reaches the target, and directed to the labelled tissue.

The type of recipient cells used to incorporate the radiation inducible genetic constructs are selected based on the objective of the treatment. In an exemplary embodiment, LAK cells are used for patients in which tumor-directed attack is the main objective. In another embodiment, endothelial cells are used to deliver genes for gene therapy, for example, to treat genetically abnormal fetuses with a metabolic deficiency or abnormality. Cells derived from peripheral blood are also suitable recipient cells.

In an exemplary embodiment of the genetic construct, there are several steps leading to expression of the structural gene in the host tissues. In these constructs, there is a radiation sensitive promoter which causes (drives) the expression of a transcription factor. The transcription factor activates a reporter construct which includes an effector appropriate for the disease or condition of the host. The expression production of the effector gene interacts in a therapeutic fashion with the diseased, deficient or abnormal cells within a target tissue.

In an exemplary embodiment, toxins which are capable of killing tumor cells are put into LAK cells or other cellular/molecular vehicles by incorporating into the cells a vector comprising a radiation inducible or responsive promoter-enhancer region and a structural gene region. Examples of a radiation responsive promoter-enhancer region comprise that derived from, for example, c-jun or TNF-α. Examples of structural genes comprise those expressed as tumor necrosis factor (TNF), ricin, or various growth factors including, but not limited to, IL-1-6, PDGF (platelet derived growth factor) or FGF (fibroblast growth factor). Diseases for which this embodiment of a construct is useful comprise cancers. Types of cancers which would benefit from this form of treatment comprise solid and hematologic malignancies. Specific cancers include head and neck adenocarcinomas.

An embodiment of a genetic construct comprises a radiation sensitive promoter coupled to an appropriate reporter, for example, β-galactosidase. The construct is transferred to a recipient cell. In general, many recipient cells are prepared in this fashion. The recipient cells are then introduced into a mammal. In an illustrative example, endothelial cells are used as the recipient cells. These cells are then transplanted into an appropriate blood vessel in which the action of the construct within the cells is desired. Radiation is delivered to an area of the body including that blood vessel. Expression of the β-galactosidase is monitored by chromogenic assays such as Xgal.

An embodiment of a structural gene which acts as a reporter-effector gene comprises that which is expressed as the tumor necrosis factor (TNF). Increased TNF-α production by human sarcomas after x-irradiation is evidence for the direct cytotoxic effects of this polypeptide on human tumor cells (Sugarman, 1985; Old, 1985). The intracellular production of TNF-α within irradiated tumor cells results in lethality to the cell after x-ray exposure that is greater than the lethality produced by the direct effects of ionizing radiation alone.

The additive and synergistic effects, the latter occurring if TNF is provided before radiation, of TNF-α on tumor killing by radiation supports potential applications for the use of TNF-α in clinical radiotherapy. TNF-α potentiates the cellular immune response (Bevelacqua, et al., 1989; Sersa, et al., 1988). In vivo studies have shown that TNF-α enhances tumor control by x-rays in mice with implanted syngeneic tumors by the augmentation of the host's immune system (Sersa, et al., 1988). Therefore, TNF-α may reverse immune suppression, which often accompanies radiotherapy. TNF-α also causes proliferation of fibroblasts and endothelial destruction, suggesting that TNF-α production by tumors may be one component responsible for the late radiation effects in surrounding normal tissue. Turning on this gene within a genetic construct by radiation allows directed attack on diseased tissues.

In addition to killing tumor cells by treatment with TNF, a goal is to protect normal tissues adjacent to the target tissue from radiation effects and deleterious action of various cytotoxins during cancer or other therapy. Solid and hemologic malignancies and aplastic anemia, are conditions for which this is a concern. Genes in the structural region of the genetic construct of this invention that are appropriate for this protective goal, include lymphokines, GCSF, CMSF, and erythropoietin.

The goal of cancer treatment is not only to kill cells at a specific target, but to inhibit metastasis. For this purpose, one of the genes appropriate for inclusion in the genetic construct is NM23.

Prevention of secondary malignancies which are an unfortunate side effect of standard radiotherapy and chemotherapy, is assisted by treatment with a construct comprising tumor suppressor genes.

This invention has uses in diseases and conditions other than cancer. For patients with clotting disorders, Factor VIII or other factors necessary for the complex process of clot formation, may be introduced into cells deficient for the missing factor.

In conditions such as myocardial infarction, central nervous system or peripheral thrombosis, anticlotting factors introduced via the genetic constructs of this invention, are used to dissolve the clots. Embodiments of the expression products of such genes include streptokinase and urokinase.

Other categories of diseases or conditions for which there is a metabolic deficiency due to either a genetic or environmental factor, include the hemoglobinopathies such as sickle cell anemia, for which genes producing normal hemoglobin are included in the treatment construct; neurodegenerative diseases such as Alzheimer's disease for which genes expressed as nerve growth factors are included in the construct; and diabetes, for which insulin producing genes may be included in the construct.

Genetic diseases caused by defects in the genetic pathways effecting DNA repair, e.g., ataxia telangiectasia, xeroderma pigmentosum, are treated by the introduction of genes such as ERCC-1 or XRCC-1.

Although the practice of this invention requires exposure to radiation, an agent which in itself may adversely affect cells, the dose is relatively low, administered for brief periods of time, and focused. For many of the diseases and conditions for which this invention is appropriate, radiation treatment is standard, and practice of this invention will reduce the necessary dose, which reduces risk of the radiation treatment per se. For diseases which usually do not require radiation, use of radiation in the methods described in this invention will replace another therapy. Decision on use of this invention will be based on a risk/benefit analysis.

DEFINITIONS

Effector Gene—a gene whose expression product produces the desired effect in the recipient cells and target tissues.

Enhancer Gene or Element—a cis- acting nucleic acid sequence that increases the ulitization of some eukaryotic promoters, and can function in either orientation and in any location (upstream or downstream) relative to the promoter.

LAK Cells—lymphocyte activated killer cells.

Promoter—a region of DNA involved in binding RNA polymerase to initiate transcription.

Reporter Gene—a gene whose expression product is readily detectable and serves as a marker for the expression of induction.

Structural Gene—a gene coding for a protein with an effector function. This protein might be an enzyme, toxin, ligand for a specific receptor, receptor, nucleic acid binding protein or antigen. The protein could also serve as a reporter to monitor induction by ionizing radiation. The gene coding for these proteins could be derived from a eukaryotic plant or animal or a prokaryote.

BRIEF DESCRIPTION OF THE DRAWINGS

Other objects and advantages of the invention will become apparent upon reading the following detailed description and upon reference to the drawings in which:

FIG. 3. A schematic drawing comprising the basic system of a retroviral mode of infection of a genetic construct into a cell.

FIGS. 6A and 6B. Effects of ionizing radiation on c-jun RNA levels in human HL-60 cells.

FIG. 8. Effects of ionizing radiation on rates of c-jun gene transcription.

FIG. 9. Effects of cycloheximide on c-jun mRNA levels in ionizing radiation-treated HL-60 cells.

Figure 1:
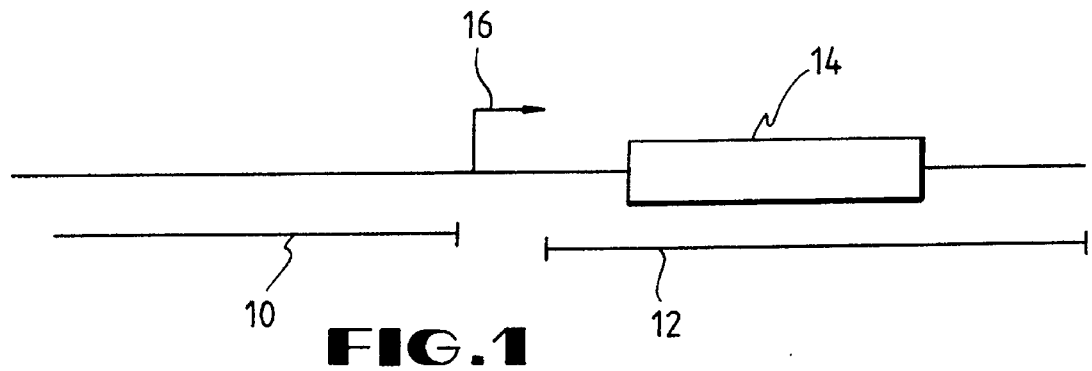
FIG. 1. A schematic drawing of the basic genetic construct comprising a radiation sensitive promoter driving an effector gene.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

This invention relates to methods and compositions of controlling expression of at least one gene by exposure of a construct, including the gene, to ionizing radiation. The genes to be controlled are preferably incorporated within a genetic construct which includes a region which is sensitive to ionizing radiation. A schematic diagram of such a construct is shown in FIG. 1 wherein an enhancer-promoter region 10 of a radiation responsive gene, e.g., c-jun, drives 16 the expression 12 of a structural gene, e.g., a reporter-effector gene such as TNF 14. The product of the structural gene expression is then capable of acting on a cell which has incorporated it, to produce a desired effect on the cell.

Figure 2A:
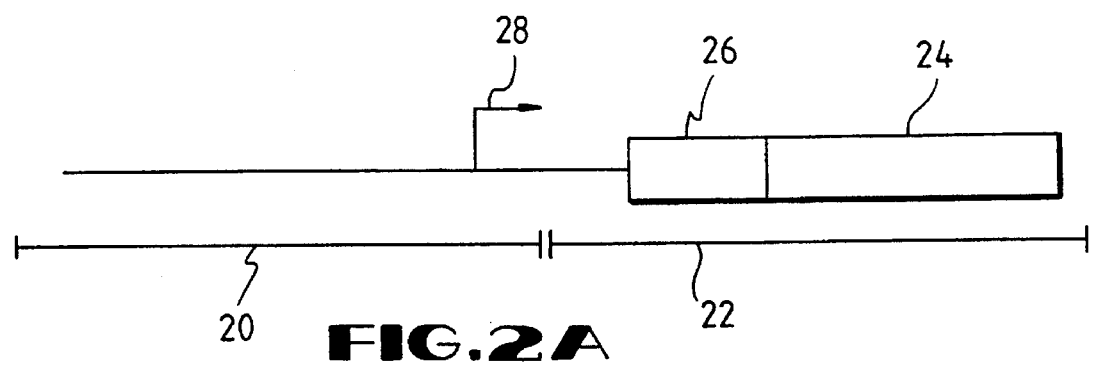
FIGS. 2A and 2B. Schematic drawings of a more complex genetic construct than that shown in FIG. 1, comprising an "amplification system."
Figure 2B:
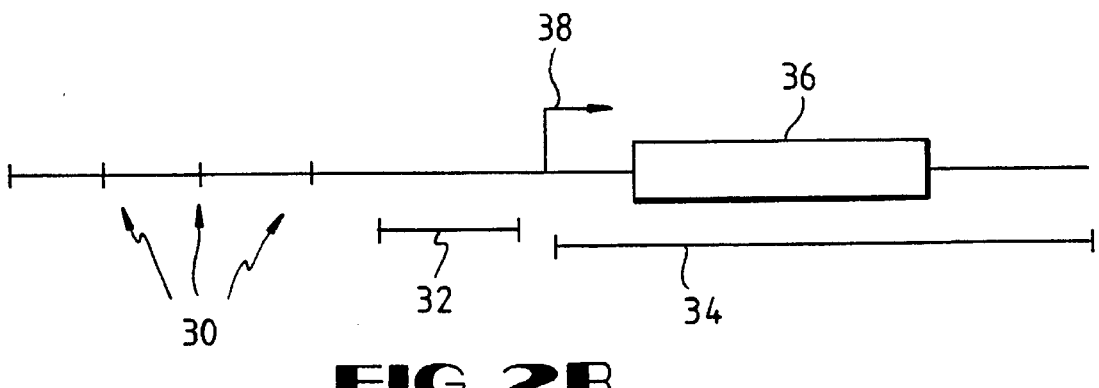

A more complex genetic construct is shown schematically in FIG. 2. In FIG. 2A, a region 20 comprising an enhancer-promoter of a radiation responsive gene, is coupled to, and drives 28 the expression of a DNA binding domain 26, e.g., of a LAC repressor gene, and a gene 24 producing a transcription factor, e.g., from VP16. The chimeric protein resulting from the expression of that fusion gene, 22 is capable of binding to a DNA sequence 30 illustrated in FIG. 2B. Binding of this sequence by the transcription factor 22 activates 38 a structural gene 36, e.g., a reporter-effector gene such as TNF. A "minimal promoter" 32 containing CCAAT and the TATA boxes, e.g., from the c-fos oncogene, is placed between the binding sequence 30 and the genes 36 to be expressed. The gene product 34 is capable of acting on a cell which has incorporated the genetic constructs, to produce a desired effect.

An example showing details of the multiple gene form of genetic construct is shown in FIG. 2. This figure is predicated on strong induction of the c-jun gene in various different cell types by ionizing radiation at a transcriptional level. A large piece of 5' genomic sequence from the jun gene is ligated to an appropriate reporter such as β-galactosidase. Such a construct is then transfected into a recipient cell and checked for radiation responsiveness. Various truncations of this initial large 5' piece may be used.

Methods of incorporating constructs into recipient cells comprise electroporation, lipofection, and viral infection. This latter method is illustrated in FIG. 3 and comprises a SIN (self-inactivating virus) with two LTR's 50, 56. Nested between the LTR's is a genetic construct comprising a radiation sensitive element 52 which drives 53 a structural gene region expressed as a gene product 54. A U3 enhancer deletion is shown at 58.

Examples of elements used for the constructs follow.

Radiation Regulates TNF-α Expression

Combinations of tumor necrosis factor α (TNF-α), a polypeptide mediator of the cellular immune response with pleiotropic activity, and radiation produce synergistic effects and are useful for clinical cancer therapy. TNF-α acts directly on vascular endothelium to increase the adhesion of leukocytes during the inflammatory process (Bevelacqua, et al., 1989). This in vivo response to TNF-α was suggested to be responsible for hemorrhagic necrosis and regression of transplantable mouse and human tumors (Carswell, 1975). TNF-α also has a direct effect on human cancer cell lines in vitro, resulting in cell death and growth inhibition (Sugarman, et al., 1985; Old, 1985). The cytotoxic effect of TNF-α correlates with free-radical formation, DNA fragmentation, and microtubule destruction (Matthews, et al., 1988; Rubin, et al., 1988; Scanlon, et al., 1989; Yamauchi, et al., 1989; Matthews, et al., 1987; Neale, et al., 1988). Cell lines that are resistant to oxidative damage by TNF-α also have elevated free-radical buffering capacity (Zimmerman, et al., 1989; Wong, et al., 1988).

TNF-α causes hydroxyl radical production in cells sensitive to killing by TNF-α (Matthews, et al., 1987). Cell lines sensitive to the oxidative damage produced by TNF-α have diminished radical-buffering capacity after TNF-α is added (Yamauchi, et al., 1989). Lower levels of hydroxyl radicals have been measured in cells resistant to TNF-α cytotoxicity when compared with cells sensitive to TNF-α killing (Matthews, et al., 1987).

Tumor necrosis factor α is increased after treatment with x-rays in certain human sarcoma cells. The increase in TNF-α mRNA is accompanied by the increased production of TNF-α protein.

The induction of a cytotoxic protein by exposure of cells containing the TNF gene to x-rays was suspected when medium decanted from irradiated cultures of some human sarcoma cell lines was found to be cytotoxic to those cells as well as to other tumor cell lines. The level of TNF-α in the irradiated tumor cultures was elevated over that of nonirradiated cells when analyzed by the ELISA technique (Saribon, et al., 1988). Subsequent investigations showed that elevated TNF-α protein after irradiation potentiates x-ray killing of cells by an unusual previously undescribed mechanism (see Example 1).

Figure 4A:
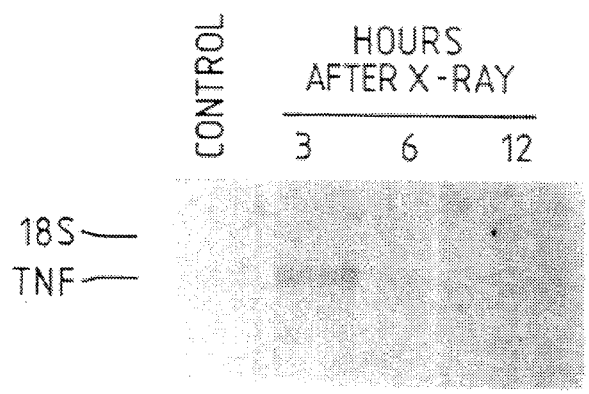
FIG. 4. Effects of irradiation on TNF-α gene expression.
Figure 4B:
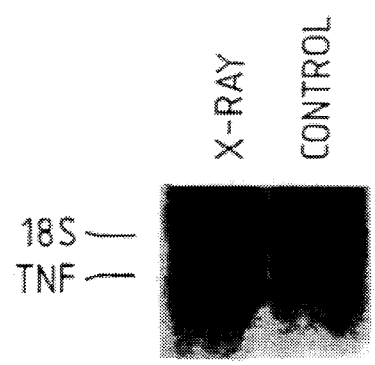

FIG. 4 illustrates the effects of irradiation on TNF-α gene expression. RNA from untreated cells (control) and irradiated cells was size-fractionated and hybridized to $^{32}$P-labeled TNF-α cDNA (STSAR-13) and PE4 plasmid containing TNF-α cDNA (STSAR-48). Autoradiograms showed increased expression of TNF-α mRNA 3 hr after irradiation in cell line STSAR-13 and at 6 hr in cell line STSAR-48. 7S RNA was hybridized to show the pattern for equally loaded lanes. The conclusion from these results is that there is increased TNF-α gene expression after radiation.

As can be seen from these results and from information discussed in EXAMPLE 1, the tumor necrosis factor α is increases after treatment with x-rays. Both mRNA and TNF-α proteins were increased.

Figure 5A:
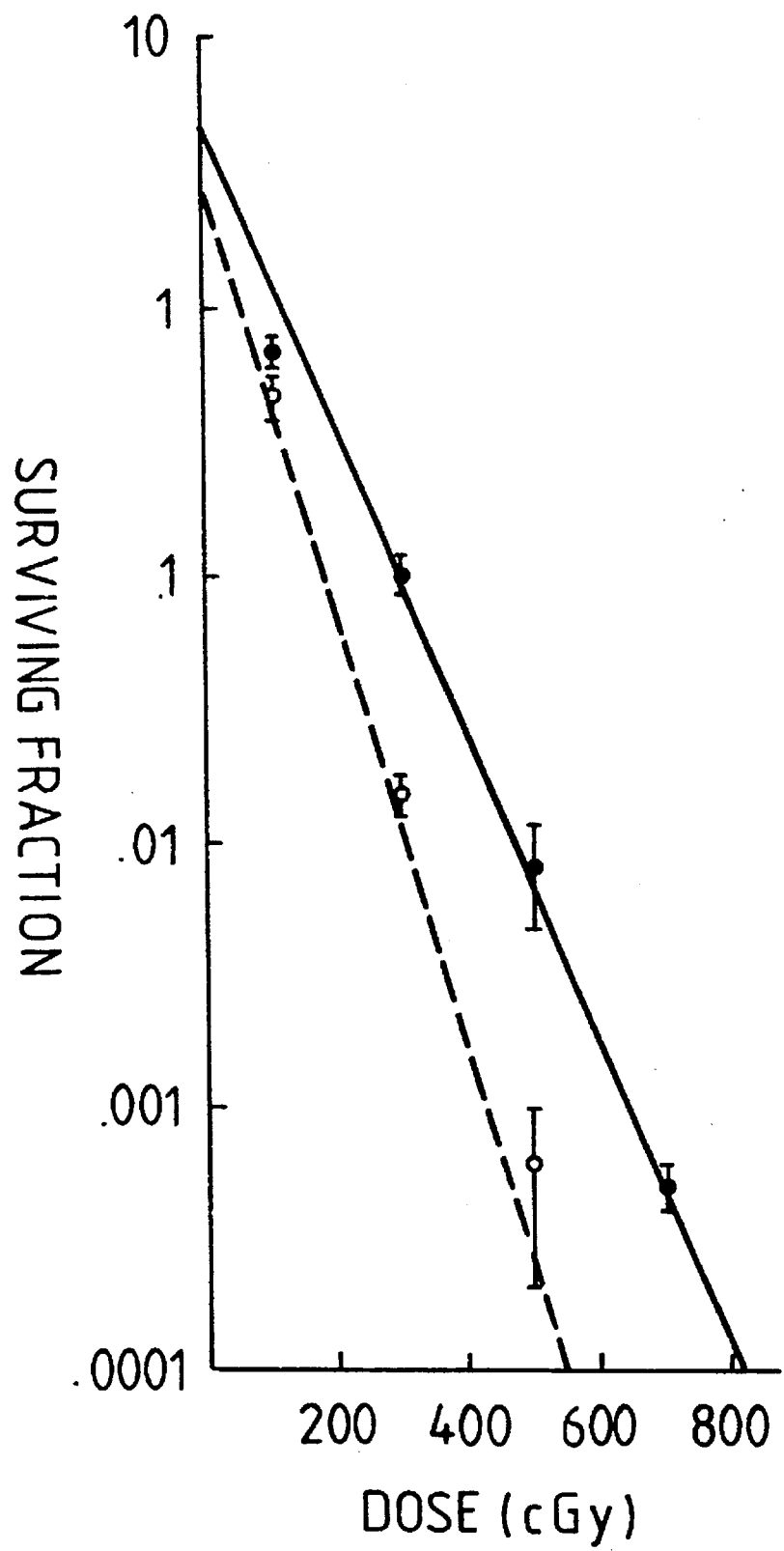
FIG. 5. Influence of TNF-α on radiation lethality of TNF-α-producing human sarcomas and TNF-α-nonproducing human tumor cells.
Figure 5B:
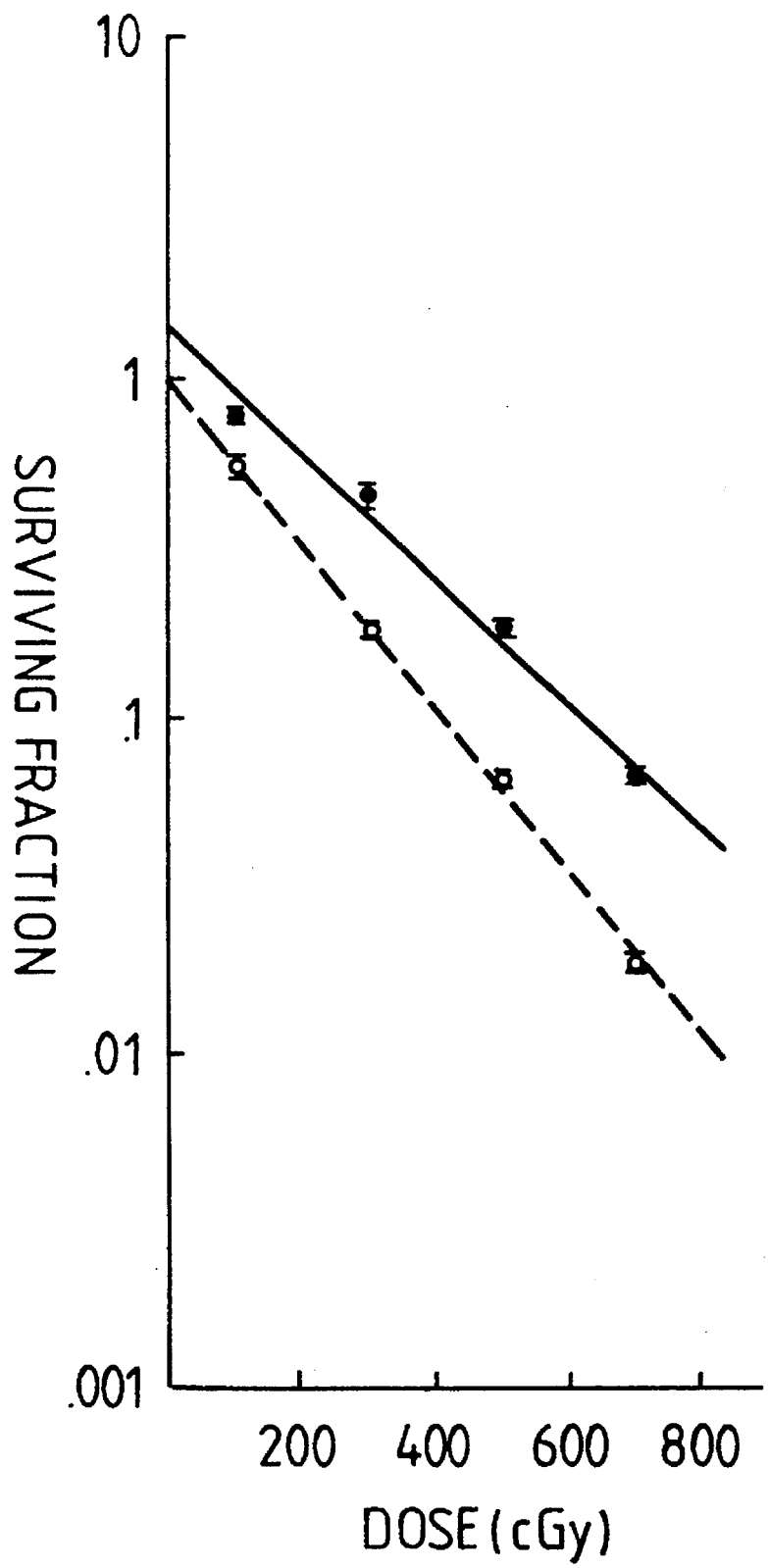
Figure 5C:
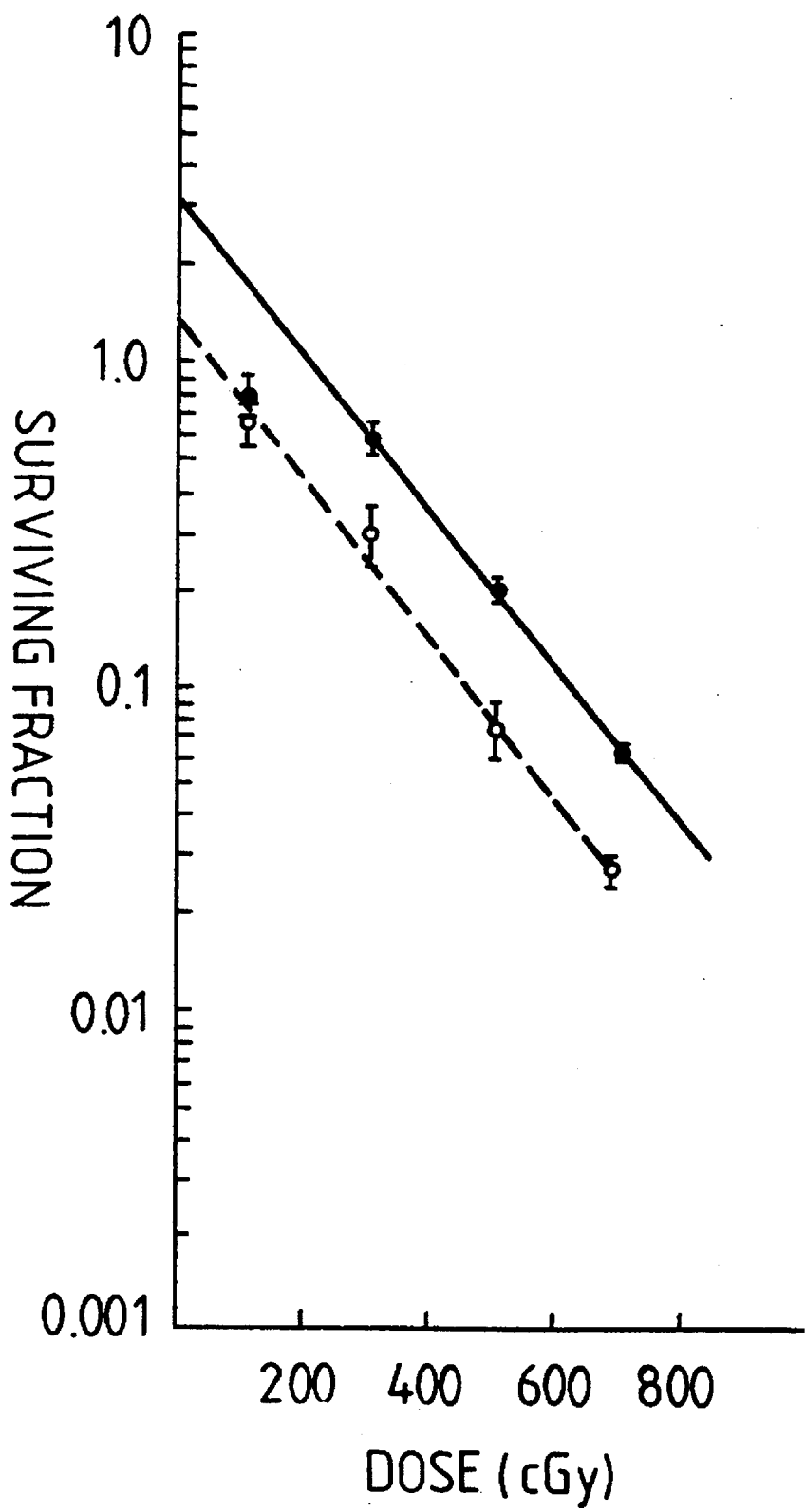

The next question was what the effects of TNF-α and radiation would be on cell killing. FIG. 5 exhibits the influence of TNF-α on radiation lethality of TNF-α-producing human sarcomas and TNF-α-nonproducing human tumor cells. The solid lines indicate the effects of radiation alone, and the dashed lines indicate the effects of both TNF-α and irradiation. Representative survival data for cell line STSAR-33 are shown in the graph to the left, A. The lower dashed line represents survival of cells with TNF-α at 1000 units/ml, corrected for a plating efficiency (PE) of 30%. The survival of human epithelial tumor cells (SQ-20B) irradiated with TNF-α (10 units/ml and 1000 units/ml) is shown in the middle graph, B. Survival data for SQ-20B show an additive effect of TNF-α (1000 units/ml). Survivals with TNF-α are corrected for 85% killing with TNF-α alone. Radiation survival data for HNSCC-68 is shown in the graph to the right, C. A nonlethal dose of TNF-α (10 units/ml) was added 24 hr before irradiation.

Although DNA-damaging agents other than ionizing radiation have been observed to induce expression of variety of prokaryotic and mammalian genes, the TNF-α gene is the first mammalian gene found to have increased expression after exposure to ionizing radiation. This gene is not categorized as a DNA repair gene.

Radiation Regulates c-jun Expression

Another embodiment of a genetic construct derives from the c-jun protooncogene and related genes. Ionizing radiation regulates expression of the c-jun protooncogene, and also of related genes c-fos and jun-β. The protein product of c-jun contains a DNA binding region that is shared by members of a family of transcription factors. Expression level after radiation is dose dependent. The c-jun gene encodes a component of the AP-1 protein complex and is important in early signaling events involved in various cellular functions. AP-1, the product of the protooncogene c-jun recognizes and binds to specific DNA sequences and stimulates transcription of genes responsive to certain growth factors and phorbol esters (Bohmann, et al., 1987; Angel, et al., 1988). The product of the c-jun protooncogene contains a highly conserved DNA binding domain shared by a family of mammalian transcription factors including jun-β, jun-D, c-fos, fos-β, fra-1 and the yeast GCN4 protein.

In addition to regulating expression of the c-jun gene, c-jun transcripts are degraded posttranscriptionally by a labile protein in irradiated cells. Posttranscriptional regulation of the gene's expression is described in Sherman, et al., 1990.

Contrary to what would be expected based on previous DNA damage and killing rates for other agents, decreasing the dose rate, for example, from 14.3 Gy/min to 0.67 Gy/min. was associated with increased induction of c-jun transcripts.

FIG. 6. Effects of ionizing radiation on c-jun RNA levels in human HL-60 cells. (A) Northern blot analysis of total cellular RNA levels was performed in HL-60 cells after treatment with 20 Gy of ionizing radiation (XRT). Hybridization was performed using a $^{32}$P-labeled c-jun or actin DNA probe. (B) HL-60 cells were treated with the indicated doses of ionizing radiation. RNA was isolated after 3 hours and hybridizations were performed using $^{32}$P-labeled c-jun or β-actin DNA probes. The column labelled HL-60 represents RNA from untreated cells.

Maximum c-jun mRNA levels were detectable after 50 Gy of ionizing radiation (FIG. 6B).

Figure 7A:
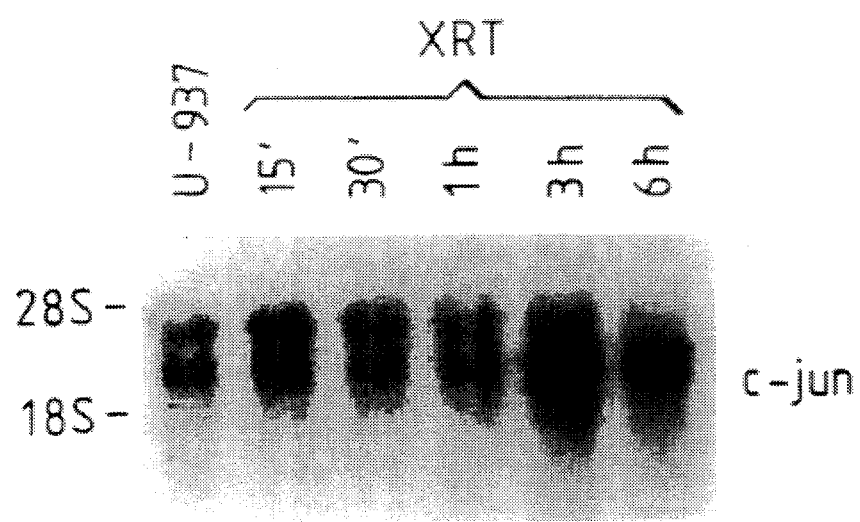
FIGS. 7A and 7B. Effects of ionizing radiation on c-jun RNA levels in U-937 cells and in human AG-1522 diploid fibroblasts.
Figure 7B:
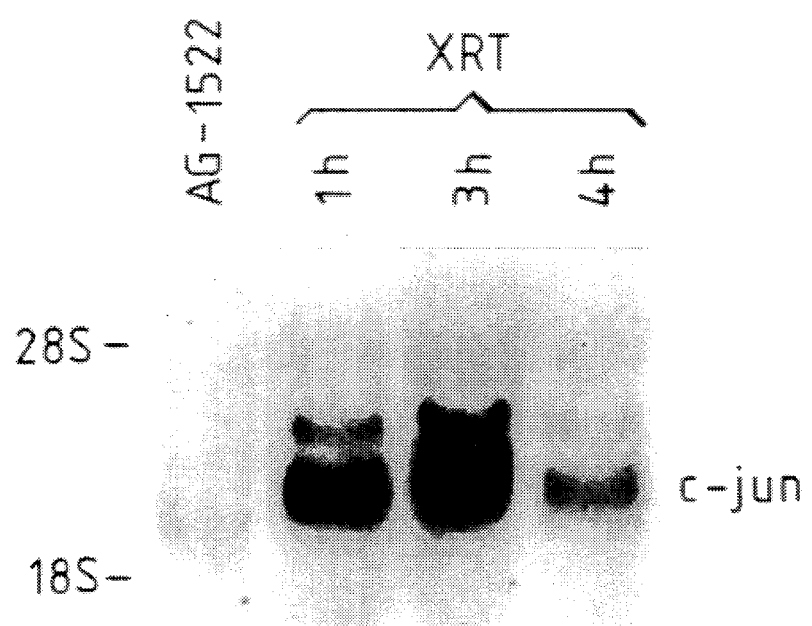

Similar kinetics of c-jun induction were observed in irradiated human U-937 monocytic leukemia cells (FIG. 7A) and in normal human AG-1522 diploid fibroblasts (FIG. 7B). Treatment of AG-1522 cells with ionizing radiation was also associated with the appearance of a minor 3.2-kb c-jun transcript.

To determine the mechanisms responsible for regulation of c-jun gene expression by ionizing radiation, run-on transcriptional assays were performed in isolated nuclei. The actin gene was constitutively transcribed in untreated HL-60 cells as a positive control (FIG. 8).

Negative control was provided by the β-globin gene transcript. As shown in FIG. 8, a low level of c-jun transcription was detectable in HL-60 untreated by radiation. Dramatic increased transcription (7.2 fold) occurred after exposure to ionizing radiation. The conclusion from this study was that ionizing radiation induced c-jun expression, at least in part by a transcriptional mechanism.

FIG. 9 illustrates the effects of cycloheximide on c-jun mRNA levels in ionizing radiation-treated HL-60 cells. HL-60 cells were treated with 20 Gy of ionizing radiation (XRT) and/or 5 μg of cycloheximide (CHX) per ml. Total cellular RNA (20 μg per lane) was isolated after 1, 3 and 6 h and analyzed by hybridization to the $^{32}$P-labeled c-jun or actin probe. The columns headed XRT shows expression of mRNA after 20 Gy radiation exposure of the cells. In the columns CHX, cycloheximide has been added. The additive effects of CHX and CHX/XRT are a 3.6 fold increased expression compared to XRT alone.

Figure 10A:
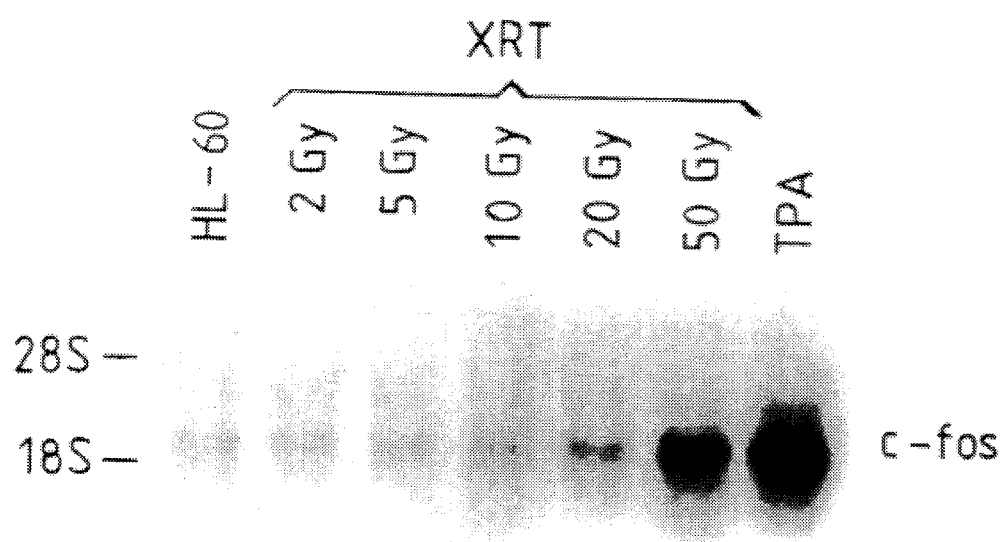
FIG. 10. Effects of ionizing radiation on C-fos and jun-B mRNA levels in HL-60 cells.
Figure 10B:
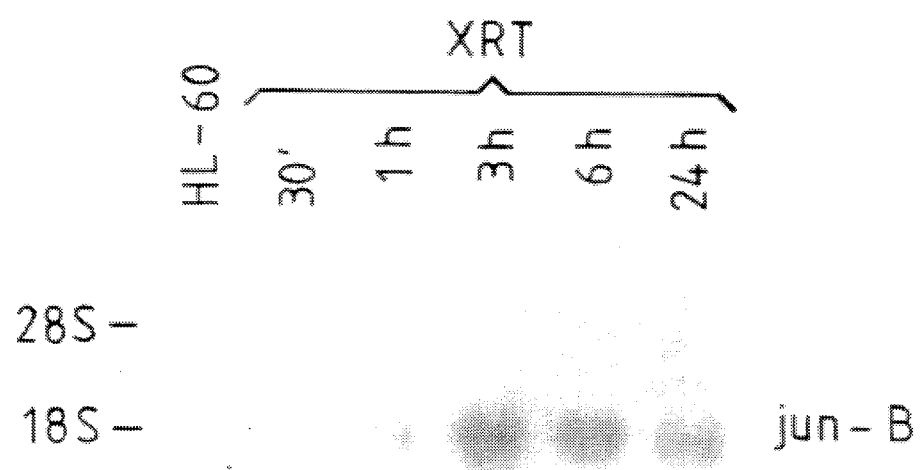

FIG. 10. Effects of ionizing radiation on C-fos and jun-B mRNA levels in HL-60 cells. (A) HL-60 cells were treated with varying doses of ionizing radiation (XRT) or 32 nM 12-O-tetradecanoylphorbol 13-acetate (TPA; positive control) for 3 h. Total cellular RNA (20 μg) was hybridized to the $^{32}$P-labeled c-fos probe. (B) HL-60 cells were treated with 20 Gy of ionizing radiation. Total cellular RNA (20 μg per lane) was isolated at the indicated times and analyzed by hybridization to the $^{32}$P-labeled jun-B probe.

Figure 11:
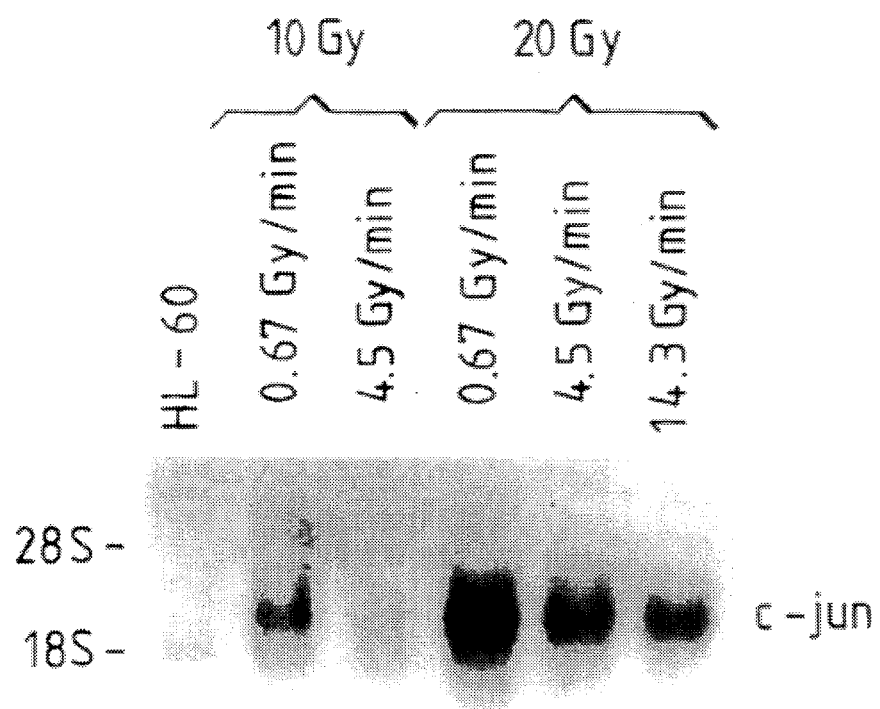
FIG. 11. Effects of dose rate on the induction of c-jun expression by ionizing radiation.

FIG. 11. Effects of dose rate on the induction of c-jun expression by ionizing radiation. HL-60 cells were treated with 10 or 20 Gy of ionizing radiation at the indicated dose rates. After 3 h, total cellular RNA (20 μg) was isolated and hybridized to the $^{32}$P-labelled c-jun probe.

Targeting Tissues for Incorporation of a Genetic Construct Responsive to Ionizing Radiation Depending on the application in question, the recipient cells are targeted in various ways. In an exemplary embodiment, LAK cells which tend to home in on the tumor site in question with some degree of preference though as is well known, they will also distribute themselves in the body in other locations, may be used to target tumors. Indeed, one of the most important advantages of the radiation inducible system is that only those LAK cells, which are in the radiation field will be activated and will have their exogenously introduced lymphokine genes activated. Thus, for the case of LAK cells, there is no particular need for any further targeting. In other applications, the appropriate cells in question have had appropriate genes from monoclonal antibodies introduced in them or appropriate antibodies expressed on their cell surface by other means such as by cell fusion. These monoclonal antibodies, for example, are targeted towards specific cells in the body and thus allow the recipient cells to home in on that particular region so that then radiation could be used for the activation of the appropriate toxins within them. This enables local delivery of the "drug," wherein the "drug" is defined as the expression product of the genes within the radiation responsive genetic construct. Illustrative embodiments of types of radiation inducible constructs and their applications are presented in Table 1 and EXAMPLE 4.

TABLE 1

ILLUSTRATIVE EMBODIMENTS OF TYPES OF RADIATION INDUCIBLE GENETIC CONSTRUCTS AND THEIR USES

| Action of Expression Products of Genes in the Construct | Example of Structural Genes Used in the Construct | Applications to Diseases Conditions, and Tissues |
|---|---|---|
| Kill tumor cells | Toxins<br>TNF<br>Growth Factors (IL-1-6 PDGF, FGF) | Solid & Hematologic Malignancies |
| Protect normal tissues from radiation and other cytotoxins during cancer therapy | Lymphokines GCSF, CMCSF<br>Erythropoietin | Solid & Hematologic Malignancies,<br>Aplastic Anemic |
| Inhibit Metastasis | NM23 | Cancer Metastasis |
| Tumor Suppressor Gene Products | Rb p53 | Prevention of Malignancy Following Standard Radiotherapy and Chemotherapy |
| Radiosensitization<br>Chemosensitization<br>(enhance routine treatment effects) | TNF | Solid & Hematologic Malignancies |
| Correct Defects in Clotting Factors | Factor 8 | Clotting Disorders |
| Introduce Anticlotting Factors | Streptokinase<br>Urokinase | Myocardial Infarction,<br>CNS Thrombosis,<br>Pheripheral Thrombosis |
| Correct Defects Characterizing Hemoglobinopathy | Normal Hemoglobin | Sickle Cell Anemia |
| Correct Deficiencies Leading to Neurodegenerative Disease | Nerve Growth Factor | Alzheimer's Disease |
| Provide Treatment Component for Diabetes | Insulin | Diabetes |
| Disease of DNA Repair Abnormalities | ERCC-1, XRCC-1 | Ataxia Telangiectasia<br>Xeroderma Pigmentosum |

EXAMPLES

Example 1

Increased Tumor Necrosis Factor α mRNA after Cellular Exposure to Ionizing Radiation A. Protein Products To investigate TNF-α protein production after x-irradiation, the levels of TNF-α in the medium of human tumor cell lines and fibroblasts were quantified by the ELISA technique (Saribon, et al., 1988) before and after exposure to 500-cGy x-rays (Table 1). Five of 13 human bone and soft tissue sarcoma cell lines (STSAR-5, -13, -33, -43, and -48) released TNF-α into the medium after irradiation, whereas TNF-α levels were not elevated in supernatant from normal human fibroblast cell lines (GM-1522 and NHF-235) and four human epithelial tumor cell lines (HN-SCC-68, SCC-61, SCC-25, and SQ-20B) after exposure to radiation. The assay accurately measures TNF-α levels between 0.1 and 2.0 units per ml ($2.3 \times 10^6$ units/mg) (Saribon, et al., 1988). Tumor cell line STSAR-13 produced undetectable amounts of TNF-α before x-irradiation and 0.35 units/ml after x-ray exposure. Cell lines STSAR-5 and -33 responded to x-irradiation with increases in TNF-α concentrations of >5- to 10-fold; however quantities above 2 units/ml exceeded the range of the assay (Saribon, et al., 1988). Cell lines STSAR-43 and -48 demonstrated increases in TNF-α of 1.5- to 3-fold (Table 1). TNF-α protein in the medium was first elevated at 20 hr after x-ray treatment, reached maximal levels at 3 days, and remained elevated beyond 5 days. Furthermore, supernatant from irradiated, but not control STSAR-33, was cytotoxic to TNF-α-sensitive cell line SQ-20B.

TABLE 2

PRODUCTION OF TNF-A IN HUMAN SARCOMA CELL LINES

| | | TNF-α level, units/ml, | |
|---|---|---|---|
| Cell Line | Origin | Control | X-ray |
| STSAR-5 | MFH | 0.4 | >2.0 |
| STSAR-13 | Liposarcoma | 0.0 | 0.34 |
| STSAR-33 | Ewing sarcoma | 0.17 | >2.0 |
| STSAR-43 | Osteosarcoma | 0.41 | 1.3 |
| STSAR-48 | Neurofibrosarcoma | 0.28 | 0.43 |

TNF-α levels were measured in medium from confluent cell cultures (control) and in irradiated confluent cells (x-ray). TNF-α levels increased as measured by the ELISA technique. MFH, malignant fibrous histiocytoma.

B. RNA Analysis

Increased levels of TNF-α mRNA were detected in the TNF-α-producing sarcoma cell lines after irradiation relative to unirradiated controls (FIG. 4). For example, TNF-α transcripts were present in unirradiated STSAR-13 and -48 cell lines. TNF-α mRNA levels in cell line STSAR-13 increased by 2.5-fold as measured by densitometry 3 hr after exposure to 500 cGy and then declined to baseline levels by 6 hr (FIG. 4). These transcripts increased at 6 hr after irradiation in cell line STSAR-48, thus indicating some heterogeneity between cell lines in terms of the kinetics of TNG-α gene expression (FIG. 4). In contrast, irradiation had no detectable effect on 7S RNA levels (FIG. 4) or expression of the polymerase β gene.

C. Interaction Between TNF-α and X-Irradiation

To investigate the influence of TNF-α on radiation-induced cytotoxicity in TNF-α-producing cell lines, recombinant human TNF-α was added to cultures before irradiation (FIG. 5). Recombinant human TNF-α (1000 units/ml) ($2.3 \times 10^6$ units/mg) was cytotoxic to four of five TNF-α-producing sarcomas (STSAR-5, -13, -33, and -43). The plating efficiency (PE) was reduced by 60–90% at 1000 units/ml in these lines. Radiation-survival analysis of cell line STSAR-33 was performed with TNF-α (10 units/ml). The radiosensitivity ($D_0$), defined as the reciprocal of the terminal slope of the survival curves was 80.4 cGy for cell line STSAR-33. When TNF-α was added 20 hr before irradiation, the $D_0$ was 60.4 cGy. Surviving fractions were corrected for the reduced PE with TNF-α. Thus, the interaction between TNF-α and radiation in STSAR-33 cells was synergistic (Dewey, 1989). Sublethal concentrations of TNF-α (10 units/ml) enhanced killing by radiation in cell line STSAR-33, suggesting a radiosensitizing effect of TNF-α. The surviving fraction of cell line STSAR-5 at 100–700 cGy was lower than expected by the independent killing of TNF-α and x-rays, although the $D_0$ values were similar. Thus, the interaction between TNF-α and radiation is additive (Dewey, 1979) in STSAR-5 cells. Cell lines STSAR-13 and STSAR-43 were independently killed with x-rays and TNF-α, and no interaction was observed.

To determine the possible interactions between TNF-α and x-rays in non-TNF-α producing cells, human epithelial tumor cells (SQ-20B and HNSCC-68) were irradiated 20 hr after TNF-α was added. These cell lines do not produce TNF-α in response to ionizing radiation. TNF-α (1000 units/ml) was cytotoxic to SQ-20B and SCC-61 cells, reducing the PE by 60–80%. The radiation survival of SQ-20B cells with and without TNF-α is shown in FIG. 5. The $D_0$ for cell line SQ-20B is 239 cGy. With TNF-α (1000 units/ml) added 24 hr before x-rays, the $D_0$ was 130.4 cGy. Therefore, a synergistic interaction (Dewey, 1979) between TNF-α and x-rays was demonstrated in this cell line. TNF-α added after irradiation did not enhance cell killing by radiation in cell lines SQ-20B. Nonlethal concentrations of TNF-α (10 units/ml) resulted in enhanced radiation killing in cell line HNSCC-68 (FIG. 5), providing evidence that TNF-α may sensitize some epithelial as well as mesenchymal tumor cell lines to radiation.

The following specific methods were used in Example 1.

Cell Lines. Methods of establishment of human sarcoma and epithelial cell lines have been described (Weichselbaum, et al., 1986; 1988). Culture medium for epithelial tumor cells was 72.5% Dulbecco's modified Eagle's medium/22.5% Ham's nutrient mixture F-12 [DMEM/F-12 (3:1)]5% fetal bovine serum (FBS), transferrin at 5 μg/ml/$10^{-10}$M cholera toxin/1.8×$10^{-4}$M adenine, hydrocortisone at 0.4 μg/ml/2× $10^{-11}$M triodo-L-thyronine/penicillin at 100 units/ml/streptomycin at 100 μg/ml. Culture medium for sarcoma cells was DMEM/F-12 (3:1)/20% FBS, penicillin at 100 units/ml/streptomycin at 100 μg/ml.

TNF-α Protein Assay. Human sarcoma cells were cultured as described above and grown to confluence. The medium was analyzed for TNF-α 3 days after feeding and again 1–3 days after irradiation. Thirteen established human sarcoma cell lines were irradiated with 500-centigray (cGy) x-rays with a 250-kV Maxitron generator (Weichselbaum, et al., 1988). TNF-α was measured by ELISA with two monoclonal antibodies that had distinct epitopes for TNF-α protein (Saribon, et al., 1988); the assay detects TNF-α from 0.1 to 2.0 units/ml.

RNA Isolation and Northern (RNA) Blot Analysis. Total cellular RNA was isolated from cells by using the guanidine thiocyanate-lithium chloride method (Cathala, et al., 1983). RNA was size-fractionated by formaldehyde-1% agarose gel electrophoresis, transferred to nylon membranes (GeneScreenPlus, New England Nuclear), hybridized as previously described to the 1.7-kilobase (kb) BamHI fragment of the PE4 plasmid containing TNF-α cDNA (Sariban, et al., 1988; Wang, et al., 1985), and autoradiographed for 16 days at −85° C. with intensifying screens. Northern blots were also hybridized to 7S rRNA and β-polymerase plasmids as described (Fornace, et al., 1989). Ethidium bromide staining revealed equal amounts of RNA applied to each lane. RNA blot hybridization of TNF-α was analyzed after cellular irradiation with 500 cGy. Cells were washed with cold phosphate-buffered saline and placed in ice at each time interval. RNA was isolated at 3, 6, and 12 hr after irradiation.

Treatment of Cells with X-Irradiation and TNF-α. Exponentially growing cells were irradiated by using a 250-kV x-ray generator. The colony-forming assay was used to determine cell survival (Weichselbaum, et al., 1988). The multitarget model survival curves were fit to a single-hit multitarget model $[S=1-(-e^{-D/D_0})^n]$. Concentrations of recombinant human TNF-α (10 units/ml) (2:3×$10^6$ units/mg) and (1000 units/ml) (Asahi Chemical, New York) were added 24 hr before irradiation.

Example 2

Method used to Show Increased c-jun Expression after Exposure to Ionizing Radiation The following methods were used in this example.

Cell Culture. Human HL-60 promyclocytic leukemia cells, U-937 monocytic leukemia cells (both from American Type Culture Collection), and AG-1522 diploid foreskin fibroblasts (National Institute of Aging Cell Repository, Camden, N.J.) were grown in standard fashion. Cells were irradiated using either Philips RT 250 accelerator at 250 kV, 14 mA equipped with a 0.35-mm Cu filter or a Gammacell 1000 (Atomic Energy of Canada, Ottawa) with a $^{137}$Cs source emitting at a fixed dose rate of 14.3 Gy/min as determined by dosimetry. Control cells were exposed to the same conditions but not irradiated.

Northern Blot Analysis. Total cellular RNA was isolated as described (Sherman, et al., 1990). RNA (20 μg per lane) was separated in an agarose/formaldehyde gel, transferred to a nitrocellulose filter, and hybridized to the following $^{32}$P-labeled DNA probes: (i) the 1.8-kilobase (kb) BamHI/EcoRI c-jun cDNA (Hattari, et al., 1988); (ii) the 0.91-kb Sca I/Nco I c-fos DNA consisting of exons 3 and 4 (van Straaten, et al., 1983); (iii) the 1.8-kb EcoRI jun-B cDNA isolated from the p465.20 plasmid (Ryder, et al., 1988); and (iv) the 2.0-kb PstI β-actin cDNA purified from pa1 (Cleveland, et al., 1980). The autoradiograms were scanned using an LKB UltroScan XL laser densitometer and analyzed using the LKB GelScan XL software package. The intensity of c-jun hybridization was normalized against β-actin expression.

Run-On Transcriptional Analysis. HL-60 cells were treated with ionizing radiation and nuclei were isolated after 3 hours. Newly elongated $^{32}$P-labeled RNA transcripts were hybridized to plasmid DNAs containing various cloned inserts after digestion with restriction endonulceases as follows: (i) the 2.0-kb Pst I fragment of the chicken β-actin pal plasmid (positive control); (ii) the 1.1-kb BamHI insert of the human β-globin gene (negative control, ref.34); and (iii) the 1.8-kb BamHI/EcoRI fragment of the human c-jun cDNA from the pBluescript SK(+) plasmid. The digested DNA was run in a 1% agarose gel and transferred to nitrocellulose filters by the method of Southern. Hybridization was performed with $10^7$ cpm of $^{32}$P-labeled RNA per ml of hybridization buffer for 72 h at 42° C. Autoradiography was performed for 3 days and the autoradiograms were scanned as already described.

Example 3

Radiation Induced Transcription of JUN and EGR1

There was increased mRNA expression for different classes of immediate early response to radiation genes (JUN, EGR1) within 0.5 to 3 hours following cellular x-irradiation. Preincubation with cycloheximide was associated with superinduction of JUN and EGR1 in x-irradiated cells. Inhibition of protein kinase C (PKC) activity by prolonged stimulation with TPA or the protein kinase inhibitor H7 prior to irradiation attenuated the increase in EGR1 and JUN transcripts. These data implicated EGR1 and JUN as signal transducers during the cellular response to radiation injury and suggested that this effect is mediated in part by a protein kinase C (PKC) dependent pathway.

JUN homodimers and JUN/FOS heterodimers regulate transcription by binding to AP1 sites in certain promoter regions (Curran and Franza, 1988). The JUN and FOS genes are induced following x-ray exposure in human myeloid leukemia cells indicating that nuclear signal transducers participate in the cellular response to ionizing radiation.

EGR1 (also known as zif/268, NGFI-1, Krox-24, TIS-8) (Christy, et al., 1988; Milbrant, 1987; Lemaire, et al., 1988; Lim, et al., 1987) encodes a nuclear phosphoprotein with a $Cys_2$-$His_2$ zinc-finger motif which is partially homologous to the corresponding domain in the Wilms' tumor susceptibility gene (Gessler, 1990). The EGR1 protein binds with high affinity to the DNA sequence CGCCCCCGC in a zinc-dependent manner (Christy and Nathans, 1989; Cao, 1990). EGR1 represents an immediate early gene which is induced during tissue injury and participates in signal transduction during cellular proliferation and differentiation.

The EGR1 and JUN genes are rapidly and transiently expressed in the absence of de novo protein synthesis after ionizing radiation exposure. EGR1 and JUN are most likely involved in signal transduction following x-irradiation. Down regulation of PKC by TPA and H7 is associated with attenuation of EGR1 and JUN gene induction by ionizing radiation, implicating activation of PKC and subsequent induction of the EGR1 and JUN genes as signaling events which initiate the mammalian cell phenotypic response to ionizing radiation injury.

Control RNA from unirradiated cells demonstrated low but detectable levels of EGR1 and JUN transcripts. In contrast, EGR1 expression increased in a dose dependent manner in irradiated cells. Levels were low but detectable after 3 Gy and increased in a dose dependent manner following 10 and 20 Gy. Twenty Gy was used in experiments examining the time course of gene expression so that transcripts were easily detectable. Cells remained viable as determined by trypan dye exclusion during this time course. A time dependent increase in EGR1 and JUN mRNA levels was observed. SQ-20B cells demonstrated coordinate increases in EGR1 and JUN expression by 30 minutes after irradiation that declined to baseline within 3 hours. In contrast, EGR1 transcript levels were increased over basal at 3 hours while JUN was increased at one hour and returned to basal at 3 hours in AG1522. JUN levels were increased at 6 hours in 293 cells while EGR1 was increased at 3 hours and returned to basal levels by 6 hours.

To determine whether EGR1 and JUN participated as immediate early genes after x-irradiation, the effects of protein synthesis inhibition by CHI were studied in cell lines 293 and SQ-20B after x-ray exposure. CHI treatment alone resulted in a low but detectable increase in EGR1 and JUN transcripts normalized to 7S. In the absence of CHI, the level of EGR1 and JUN expression returned to baseline. In contrast, SQ-20B cells pretreated with CHI demonstrated persistent elevation of EGR1 at 3 hours and 293 cells demonstrated persistent elevation of JUN mRNA at 6 hours after irradiation thus indicating superinduction of these transcripts.

mRNA levels of transcription factors EGR1 and JUN increased following ionizing radiation exposure in a time and dose dependent manner. The potential importance of the induction of EGR1 and JUN by ionizing radiation is illustrated by the recent finding that x-ray induction of the PDGF alpha chain stimulates proliferation of vascular endothelial cells (Witte, et al., 1989). PDGF has AP-1 and EGR1 binding domains while TNF has elements similar to AP-1 and EGR1 target sequences (Rorsman, et al., 1989; Economou, et al., 1989). X-ray induction of PDGF and TNF appears to be regulated by EGR1 and JUN.

The following is a method used in Example 3:
Kinase Inhibitors

Cell line SQ-20B was pretreated with 1 µM TPA for 40 hours to down regulate PKC and then stimulated with TPA, serum, or x-ray (20 Gy). Controls included x-ray without TPA pretreatment, TPA (50 nM) without TPA pretreatment and untreated cells. RNA was isolated after one hour and hybridized to EGR1. SQ-20B cells were preincubated with 100 µM H7 (1-(5-isoquinolinylsulfonyl)-2-methyl piperazine) or 100 µM HA1004 (N-[2-methyl-amino] ethyl)-5-isoquinolinesulfonamide) Seikagaku America, Inc., St. Petersberg, Fla.) for 30 minutes or TPA pretreatment (1 µM) for 40 hours and followed by exposure to 20 Gy x-irradiation. RNA was extracted one hour after irradiation. Positive control cells treated under the same conditions but in the absence of inhibitor also received 20 Gy, while negative control cells received neither H7 nor X-ray. RNA was extracted at one hour after 20 Gy without inhibitor. Northern blots were hybridized to EGR1 or 7S. 293 cells pretreated with the above inhibitors were irradiated, RNA was extracted after 3 hours and the Northern blot was hybridized to JUN and 7S probes.

Example 4

Protocol for Treatment of Head and Neck Cancer with X-ray Induced TNF and Therapeutic X-rays For treatment of patients with head and neck cancer, the following steps are followed:

1. Prepare a genetic construct according to the general scheme illustrated in FIGS. 1 or 2.

This construct comprises AP-1 as the element which is responsive to x-rays, coupled to a sequence of DNA to which the lac repressor binds, and to the gene for the tumor necrosis factor. This construct is designated "construct A" for purposes of this example.

2. "Construct A" is put into a retrovirus that is self-inactivating (see FIG. 3).

3. Lymphokine activated killer (LAK) cells are infected with the retrovirus bearing "construct A." The cells are to be directed against the malignant cells in the head and neck.

4. The lymphocytes are infused into the patient to be treated.

5. The head and neck region is irradiated.

REFERENCES

The references listed below are incorporated herein by reference to the extent that they supplement, explain, provide a background for, or teach methodology, techniques, and/or compositions employed herein.

Reference 1. Andrews, G. K., Harding, M. A., Calvert, J. P. and Adamson, E. D. (1987) *Mol. Cell. Biol.* 7:3452–3458.

Reference 2. Angel, P., Poting, A., Mallick, U., Rahmsdorf, H. J., Schorpp, M., and Herrlich, P. (1986) *Mol. Cell. Biol.* 6:1760–1766.

Reference 3. Angel, P., Baumann, I., Stein, B., Dallus, H., Rahmsdorf, H. J., and Herrlich, P. (1987) *Mol. Cell. Biol.* 7:2256–2266.

Reference 4. Angel, P. Allegretto, E. A., Okino, S., Hattori, K., Boyle, W. J., Hunter, T. and Karin, M. (1988) *Nature* (London) 332:166–171.

Reference 5. Bevelacqua, M. P., Stengelin, S., Gimbrone, M. A., and Seed, B. (1989) *Science* 243:1160–1165.

Reference 6. Bohmann, D., Bos, T. J., Admon, A., Nishimura, T., Vogt, P. K, and Tjian, R. (1987) *Science* 238:1386–1392.

Reference 7. Bonura, T. and Smith, K. C. (1976) *Int. J. Radiat. Biol* 29:293–296.

Reference 8. Boothman, D. A., Bouvard, I and Hughes, E. N. (1989) *Cancer Res.* 49:2871–2878.

Reference 9. Borek, C. (1985) *Pharmacol. Ther.* 27:99–142.

Reference 10. Cao, X. (1990) *Mol. Cell. Biol.* 10:1931–1939.

Reference 11. Carswell, E. A. (1975) *Proc. Natl. Acad. Sci. U.S.A.* 72:3666–3670.

Reference 12. Cathala, G., Savouret, J. F., Mendez, B., West, B. L., Karin, M., Martial, J. A. and Baxter, J. D. (1983) *DNA* 2:329–335.

Reference 13. Christy, B. A., Lau, L. F., Nathans, D. (1988) *Proc. Natl. Acad. Sci. U.S.A.* 85:7857–7861.

Reference 14. Christy, B. A. and Nathans, D. (1989) *Proc. Natl. Acad. Sci.* 86:8737–8741.

Reference 15. Cleveland, D. W., Lopata, M. A., MacDonald, R. J., Cowan, N. J., Rutter, W. J. and Kirschner, M. W. (1980) *Cell* 20:95–105.

Reference 16. Curran, T., Franza, B. R. (1988) *Cell* 55:395–397.

Reference 17. Dewey, W. C. (1979) *Int. J. Radiat. Oncol. Biol. Phys.* 5:1165–1174.

Reference 18. Economou, J. S., Rhoades, K., Essner, R., McBride, W. H., Gasson, J. C. and Morton, D. L. (1989) *J. Exp. Med.* 170:321–326.

Reference 19. Fornace, A. J., Alamo, I., and Hollander, M. C. (1988) *Proc. Natl. Acad. Sci. U.S.A.* 85:8800–8804.

Reference 20. Fornace, A. J., Jr., Schalch, H. and Alamo, I., Jr. (1988) *Mol. Cell. Biol.* 8:4716–4720.

Reference 21. Fornace, A. J., Zmudzka, B., Hollander, M. C. and Wilson, S. H. (1989) *Mol. Cell. Biol.* 9:851–853.

Reference 22. Gessler, M. (1990) *Nature* 343:774–778.

Reference 23. Hall, E. J. (1988) in *Radiobiology for the Radiologist*, ed. Hall, E. J. (Lippincott, Philadelphia), pp. 17–38.

Reference 24. Hallahan, D. E., Spriggs, D. R., Beckett, M. A., Kufe, D. W., and Weichselbaum, R. R. (1989) *Proc. Natl. Acad. Sci. U.S.A.* 86:10104–10107.

Reference 25. Hattori, K., Angle, P., LeBeau, M. M., and Karin, M. (1988) *Proc. Natl. Acad. Sci. U.S.A.* 85:9148–9152.

Reference 26. Herrlich, P. (1987) *Accomplishments in Cancer Research* (Lippincott, Philadelphia), pp. 213–228.

Reference 27. Hollander, C. M. and Fornace, A. J., Jr. (1989) *Cancer Res.* 49:1687–1693.

Reference 28. Lambert, M. and Borek, C. (1988) *J. Natl. Cancer Inst.* 80:1492–1497.

Reference 29. Lemaire, P., Relevant, O., Bravo, R., Charnay, P. (1988) *Proc. Natl. Acad. Sci. U.S.A.* 85:4691–4695.

Reference 30. Little, J. W. and Mount, D. W. (1982) *Cell* 29:11–22.

Reference 31. Lim, R. W., Varnum, B. C., Herschman, H. R. (1987) *Oncogene* 1:263–270.

Reference 32. Matthews, N., Neale, M. L., Fiera, R. A., Jackson, S. K., and Stark, S. M. (1988) *Tumor Necrosis Factor/Cachectin and Related Cytokinesis*, eds. Bonavida, B., Gifford, G. E., Kirchner, H. & Old, L. J. (Karger, N.Y.), pp. 20–25.

Reference 33. Matthews, N., Neale, M. L., Jackson, S. K. and Stark, J. M. (1987) *Immunology* 62:153–155.

Reference 34. Milbrandt, J., (1987) *Science* 238:797–799.

Reference 35. Miskin, R. and Ben-Ishai, R. (1981) *Proc. Natl. Acad. Sci. U.S.A.* 78:6236–6240.

Reference 36. Moulder, J. E. and Rockwell, S. (1984) *Int. J. Radiat. Oncol. Biol. Phys.* 10:695–712.

Reference 37. Neale, M. L., Fiera, R. A. and Matthews, N. (1988) *Immunology* 64:81–85.

Reference 38. Old, L. J. (1985) *Science* 230:630–634.

Reference 39. Papathanasiou, M., Barrett, S. F., Hollander, M. C., Alamo, J., Jr., Robbins, J. H., Fornace, A. J., Jr. (1990) *Proc. Ann. Meet. Am. Assoc. Cancer Res.* 31:A1802.

Reference 40. Rorsman, F., Bywater, M., Knott, T. J., Scott, J. and Betsholtz, C. (1989) *Mol. Cell. Biol.* 8:571–577.

Reference 41. Rubin, B. Y., Smith, L. J., Hellerman, G. R., Lunn, R. M., Richardson, N. K, and Anderson, S. L. (1988) *Cancer Res.* 48:6006–6010.

Reference 42. Ryder, K., Lau, L. F., and Nathans, D. (1988) *Proc. Natl. Acad. Sci. U.S.A.* 85:1487–1491.

Reference 43. Sariban, E., Imamura, K., Luebbers, R. and Kufe, D. (1988) *J. Clin. Invest.* 81:1506–1510.

Reference 44. Scanlon, M., Laster, S. M., Wood, J. G. & Gooding, L. R. (1989) *Cell Biol.* 86:182–186.

Reference 45. Schorpp, M., Mallick, V., Rahmsdorf, H. J. and Herrlich, P. (1984) *Cell* 37:861–868.

Reference 46. Sersa, G., Willingham, V. and Milas, L. (1988) *Int. J. Cancer* 42:129–134.

Reference 47. Sherman, M. L., Datta, R., Hallahan, D. E., Weichselbaum, R. R., Kufe, D. W. (1990) *Proc. Natl. Acad. Sci. U.S.A.* 87:5663–5666.

Reference 48. Sherman, M. L., Stone, R. M., Datta, R., Bernstein, S. H. and Kufe, D. W. (1990) *J. Biol. Chem.* 265:3320–3323.

Reference 49. Sugarman, B. J., Aggarwai, B. B., Huas, P. E., Figari, I. S., Palladino, M. A., Jr. and Shepard, H. M. (1985) *Science* 230:943–945.

Reference 50. van Straaten, F., Muller, R., Curran, T., van Beveren, C. and Verma, I. M. (1983) *Proc. Natl. Acad. Sci. U.S.A.* 80:3183–3187.

Reference 51. Wang, A. M., Creasg, A. A., Lander, M. B., Lin, L. S., Strickler, J., Van Arsdell, J. N., Yanamotot, R. and Mark, D. F. (1985) *Science* 228:149–154.

Reference 52. Weichselbaum, R. R., Nove, J. and Little, J. B. (1980) *Cancer Res.* 40:920–925.

Reference 53. Weichselbaum, R. R., Dahlberg, W., Beckett, M. A., Karrison, T., Miller, D., Clark, J. and Ervin, T. J. (1986) *Proc. Natl. Acad. Sci. U.S.A.* 83:2684:2688.

Reference 54. Weichselbaum, R. R., Beckett, M. A., Simon, M. A., McCowley, C., Haraf, D., Awan, A., Samuels, B., Nachman, J. and Drtischilo, A. (1988) *Int. J. Rad. Oncol. Biol. Phys.* 15:937–942.

Reference 55. Wilson, J. T., Wilson, L. B., deRiel, J. K., Villa-Komaroff, L., Efstratiadis, A., Forget, B. G. and Weissman, S. M. (1978) *Nucleic Acids Res.* 5:563–580.

Reference 56. Witte, L., Fuks, Z., Haimovitz-Friedman, A., Vlodavsky, I., Goodman, D. S. and Eldor, A. (1989) *Cancer Res.* 49:5066–5072.

Reference 57. Woloschak, G. E., Chang-Liu, C. M., Jones, P. S. and Jones, C. A. (1990) *Cancer Res.* 50:339–344.

Reference 58. Wong, G. W. H. and Goeddel, D. V. (1988) *Science* 242:941–943.

Reference 59. Wong, G. H. W., Elwell, J. H., Oberly, L. H., Goeddel, D. V. (1989) *Cell* 58:923–931.

Reference 60. Yamuchi, N., Karizana, H., Watanabe, H., Neda, H., Maeda, M. and Nutsu, Y. (1989) *Cancer Res.* 49:1671–1675.

Reference 61. Zimmerman, R. J., Chan, A. and Leadon, S. A. (1989) *Cancer Res.* 49:1644–1648.

What is claimed is:

1. A method for expressing a structural gene in a cell, said method comprising the steps of:
   (a) incorporating into said cell a genetic construct comprising the structural gene and a Egr, c-jun or TNF-α promoter-enhancer region inducible by ionizing radiation, the promoter-enhancer region driving the expression of the structural gene; and
   (b) exposing the cell to ionizing radiation at a dose sufficient to induce expression of the structural gene.

2. The method of claim 1 wherein said structural gene encodes TNF-α.

3. The method according to claim 1, wherein the enhancer-promoter region comprises the c-jun enhancer-promoter region.

4. The method according to claim 1 wherein the enhancer-promoter region comprises the EGR enhancer-promoter region.

5. The method according to claim 1, wherein the enhancer-promoter region comprises the TNF-α promoter-enhancer region.

6. The method according to claim 1, wherein the genetic construct is exposed to ionizing radiation by exposing a cell in vivo to said radiation.

7. The method according to claim 1, wherein the genetic construct is incorporated into a cell in vivo.

8. The method according to claim 1, wherein the ionizing radiation is delivered by an external source.

* * * * *

UNITED STATES PATENT AND TRADEMARK OFFICE
CERTIFICATE OF CORRECTION

PATENT NO. : 5,612,318

DATED : March 18, 1997

INVENTOR(S) : Weichselbaum et al.

It is certified that error appears in the above-identified patent and that said Letters Patent is hereby corrected as shown below:

At column 2, line 29, after "radiation" insert --effect--.
At column 12, line 46, change "Table 1" to --Table 2--.
At column 12, line 62, change "Table 1" to --Table 2--.

Signed and Sealed this

Twenty-fifth Day of November, 1997

Attest:

BRUCE LEHMAN

Attesting Officer

Commissioner of Patents and Trademarks